US011318223B2

(12) United States Patent
Wibaux

(10) Patent No.: US 11,318,223 B2
(45) Date of Patent: *May 3, 2022

(54) ANTIMICROBIAL ADHESIVES HAVING IMPROVED PROPERTIES

(71) Applicant: Avery Dennison Corporation, Glendale, CA (US)

(72) Inventor: Anne Marie Wibaux, Fontainebleau (FR)

(73) Assignee: Avery Dennison Corporation, Glendale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/451,671

(22) Filed: Jun. 25, 2019

(65) Prior Publication Data
US 2020/0016291 A1 Jan. 16, 2020

Related U.S. Application Data

(62) Division of application No. 14/766,524, filed as application No. PCT/US2014/015263 on Feb. 7, 2014, now Pat. No. 10,456,498.

(60) Provisional application No. 61/790,692, filed on Mar. 15, 2013, provisional application No. 61/761,838, filed on Feb. 7, 2013.

(51) Int. Cl.
| A61L 24/00 | (2006.01) |
| C09J 11/06 | (2006.01) |
| A01N 47/44 | (2006.01) |
| A61L 24/04 | (2006.01) |
| A61L 24/08 | (2006.01) |
| C09J 133/00 | (2006.01) |

(52) U.S. Cl.
CPC .......... *A61L 24/0015* (2013.01); *A01N 47/44* (2013.01); *A61L 24/001* (2013.01); *A61L 24/046* (2013.01); *A61L 24/08* (2013.01); *C09J 11/06* (2013.01); *C09J 133/00* (2013.01); *A61L 2300/206* (2013.01); *A61L 2300/404* (2013.01)

(58) Field of Classification Search
CPC .......... C09J 133/00; C09J 11/06; A61L 24/08; A61L 24/001; A61L 24/0015; A61L 24/046; A61L 2300/206; A61L 2300/404; A01N 47/44
See application file for complete search history.

(56) References Cited

U.S. PATENT DOCUMENTS

| 2,736,721 A | 2/1956 | Dexter |
| 4,199,567 A | 4/1980 | Rankin |
| 4,310,509 A | 1/1982 | Berglund et al. |
| 4,434,181 A | 2/1984 | Marks, Sr. et al. |
| 4,460,369 A | 7/1984 | Seymour |
| 4,600,001 A | 7/1986 | Gilman |
| 4,753,232 A | 6/1988 | Ward |
| 4,941,882 A | 7/1990 | Ward et al. |
| 4,990,144 A | 2/1991 | Blott |
| 5,018,516 A | 5/1991 | Gilman |
| 5,069,907 A | 12/1991 | Mixon et al. |
| 5,214,119 A | 5/1993 | Leir et al. |
| 5,270,358 A | 12/1993 | Asmus |
| 5,322,695 A | 6/1994 | Shah et al. |
| 5,340,581 A | 8/1994 | Tseng et al. |
| 5,382,451 A | 1/1995 | Johnson et al. |
| 5,389,376 A | 2/1995 | Duan et al. |
| 5,441,741 A | 8/1995 | Cheong |
| 5,614,310 A | 3/1997 | Delgado et al. |
| 5,686,096 A | 11/1997 | Khan et al. |
| 5,702,721 A | 12/1997 | Horstmann et al. |
| 5,717,005 A | 2/1998 | Richardson |
| 5,763,412 A | 6/1998 | Khan et al. |
| 5,908,693 A | 6/1999 | Delgado et al. |
| 6,043,406 A | 3/2000 | Sessions et al. |
| 6,228,354 B1 | 5/2001 | Jeng |
| 6,455,086 B1 | 9/2002 | Trinh et al. |
| 6,458,341 B1 | 10/2002 | Rozzi et al. |
| 6,495,158 B1 | 12/2002 | Buseman |
| 6,518,359 B1 | 2/2003 | Clemens et al. |
| 6,642,304 B1 | 4/2003 | Hansen et al. |
| 6,565,873 B1 | 5/2003 | Shefer et al. |
| 6,589,562 B1 | 7/2003 | Shefer et al. |
| 6,599,525 B2 | 7/2003 | Scamilla Aledo et al. |
| 6,733,745 B2 | 5/2004 | Rozzi et al. |

(Continued)

FOREIGN PATENT DOCUMENTS

| AU | 1985043241 | 12/1985 |
| CA | 1207228 | 7/1986 |

(Continued)

OTHER PUBLICATIONS

Polysciences, Poly(acrylic acid), 25% soln. in water [PAA~50,000], Retrieved Aug. 14, 2021. (Year: 2021).*

Ceballos, et al., Influence of formulation and process variables on in vitro release of theophylline from directly-compressed Eudragit matrix tablets, Il Farmaco, Jan. 15, 2005, 913-918, vol. 60, No. 11-12.

Cui, et al., Bilayer Films for Mucosal (Genetic) Immunization via the Buccal Route in Rabbits, Pharmaceutical Research, Jul. 2002, 947-953, vol. 19, No. 7.

(Continued)

*Primary Examiner* — Lezah Roberts
(74) *Attorney, Agent, or Firm* — Avery Dennison Corporation

(57) ABSTRACT

Adhesive compositions exhibiting antimicrobial properties, good stability, long shelf lives and enhanced release of antimicrobial agents are described. In certain versions, the compositions also exhibit relatively high fluid handling capacities. The adhesive compositions inhibit microbial growth by more than 2 log after 24 hours contact and particularly more than 3.5 log after 6 hours contact. Also described are various medical articles using such adhesives and related methods.

22 Claims, 1 Drawing Sheet

(56) References Cited

U.S. PATENT DOCUMENTS

| | | | |
|---|---|---|---|
| 6,742,522 | B1 | 6/2004 | Baker |
| 6,844,306 | B2 | 1/2005 | Werle et al. |
| 6,893,655 | B2 | 5/2005 | Flanigan et al. |
| 7,160,976 | B2 | 1/2007 | Luhmann et al. |
| 7,674,473 | B2 | 3/2010 | Falder et al. |
| 7,683,216 | B2 | 3/2010 | Dubois et al. |
| 7,704,523 | B2 | 4/2010 | Serafica et al. |
| 7,824,122 | B2 | 11/2010 | Flores et al. |
| 8,623,935 | B2 | 1/2014 | Hobbs et al. |
| 8,969,649 | B2 | 3/2015 | Leibowitz et al. |
| 9,101,134 | B2 | 8/2015 | Huang et al. |
| 9,278,155 | B2 | 3/2016 | Asmus et al. |
| 9,346,981 | B2 | 5/2016 | Wibaux et al. |
| 9,592,161 | B2 | 3/2017 | Rule et al. |
| 9,764,059 | B2 | 9/2017 | Wibaux et al. |
| 9,801,902 | B2 | 10/2017 | Smith et al. |
| 10,329,384 | B2 | 6/2019 | Hansen et al. |
| 2002/0018814 | A1 | 2/2002 | Werle et al. |
| 2002/0072480 | A1 | 6/2002 | Werle et al. |
| 2003/0077316 | A1 | 4/2003 | Nichols et al. |
| 2003/0212005 | A1 | 11/2003 | Petito |
| 2004/0009202 | A1 | 1/2004 | Woller |
| 2004/0063792 | A1 | 4/2004 | Khera et al. |
| 2004/0109869 | A1 | 6/2004 | Glenn et al. |
| 2004/0170794 | A1 | 9/2004 | Verhaert |
| 2004/0241214 | A1 | 12/2004 | Kirkwood et al. |
| 2005/0049365 | A1 | 3/2005 | Cleary et al. |
| 2005/0118246 | A1 | 6/2005 | Wong et al. |
| 2005/0244346 | A1 | 11/2005 | Nakao et al. |
| 2005/0249791 | A1 | 11/2005 | Hobbs et al. |
| 2007/0116729 | A1 | 5/2007 | Palepu |
| 2007/0259029 | A1 | 11/2007 | McEntire et al. |
| 2008/0220045 | A1 | 9/2008 | Shalaby et al. |
| 2008/0233177 | A1 | 9/2008 | Meconi |
| 2009/0130157 | A1 | 5/2009 | Ylitalo et al. |
| 2010/0022654 | A1 | 1/2010 | Asmus et al. |
| 2010/0029779 | A1 | 2/2010 | Street et al. |
| 2010/0081672 | A1 | 4/2010 | Wan et al. |
| 2010/0303878 | A1 | 12/2010 | Slager et al. |
| 2010/0322996 | A1 | 12/2010 | Wibaux et al. |
| 2011/0067799 | A1 | 3/2011 | Mussig et al. |
| 2012/0078155 | A1 | 3/2012 | Bowman et al. |
| 2012/0245538 | A1 | 9/2012 | Horstmann et al. |
| 2012/0328682 | A1 | 12/2012 | Bardwell et al. |
| 2013/0072566 | A1 | 3/2013 | Asmus et al. |
| 2013/0239977 | A1 | 9/2013 | McGuire, Jr. |
| 2013/0243841 | A1 | 9/2013 | Kommareddy et al. |
| 2013/0303656 | A1 | 11/2013 | Wibaux et al. |
| 2014/0322299 | A1 | 10/2014 | Wibaux |
| 2015/0056291 | A1 | 2/2015 | Wibaux et al. |
| 2015/0367021 | A1 | 12/2015 | Wibaux |
| 2016/0000609 | A1 | 1/2016 | Van Holten et al. |
| 2016/0030248 | A1 | 2/2016 | Potters |
| 2016/0228600 | A1 | 8/2016 | Wibaux et al. |
| 2017/0007464 | A1 | 1/2017 | Liu et al. |
| 2017/0095431 | A1 | 4/2017 | Andrews et al. |

FOREIGN PATENT DOCUMENTS

| | | | |
|---|---|---|---|
| CA | 2333009 | | 12/1999 |
| CN | 1522687 | | 8/2004 |
| CN | 1961666 | | 5/2007 |
| CN | 101653431 | * | 2/2010 |
| EP | 0066899 | | 12/1982 |
| EP | 0404558 | | 12/1990 |
| EP | 0328421 | | 4/1993 |
| EP | 0361722 | | 12/1993 |
| EP | 1139981 | | 4/2002 |
| EP | 1203531 | | 11/2003 |
| EP | 1784232 | | 5/2007 |
| EP | 3280769 | | 2/2018 |
| EP | 3368086 | | 9/2018 |
| EP | 2968014 | | 4/2019 |
| GB | 2274586 | | 8/1994 |
| JP | 1990-147063 | | 6/1990 |
| JP | 1994-508287 | | 9/1994 |
| JP | 1994508287 | | 9/1994 |
| JP | 6-509955 | | 11/1994 |
| JP | 2825549 | | 11/1998 |
| JP | 2002/179513 | | 6/2002 |
| JP | 2002-272831 | | 9/2002 |
| JP | 2002-332228 | | 11/2002 |
| JP | 2003/534310 | | 11/2003 |
| JP | 2004/010545 | | 1/2004 |
| JP | 2007/502319 | | 2/2007 |
| JP | 2007-526348 | | 9/2007 |
| JP | 2007-536261 | | 12/2007 |
| JP | 2014/510038 | | 4/2014 |
| WO | 1990/013780 | | 11/1990 |
| WO | 1993/00118 | | 1/1993 |
| WO | 1993/02717 | | 2/1993 |
| WO | 1993002717 | | 2/1993 |
| WO | 1993/03649 | | 3/1993 |
| WO | 1999/000025 | | 1/1999 |
| WO | 1999023150 | | 5/1999 |
| WO | 992470 | | 12/1999 |
| WO | 2000/036353 | | 6/2000 |
| WO | 2000/061692 | | 10/2000 |
| WO | 2003/103618 | | 12/2003 |
| WO | 2004/080499 | | 9/2004 |
| WO | 2009/064291 | | 5/2009 |
| WO | 2010/080936 | | 7/2010 |
| WO | 2011/009083 | | 1/2011 |
| WO | 2011/088072 | | 7/2011 |
| WO | 2012/100244 | | 7/2012 |
| WO | 2012/158483 | | 3/2013 |
| WO | 2013/074628 | | 5/2013 |
| WO | 2013/090191 | | 6/2013 |
| WO | 2014/151355 | | 9/2014 |
| WO | 2015/188031 | | 12/2015 |
| WO | 2015187632 | | 12/2015 |

OTHER PUBLICATIONS

Eudragit, acrylic polymers for solid oral dosage forms, Jan. 1, 2008, 1-11.

International Search Report and Written Opinion issued in corresponding IA No. PCT/US2014/025549 dated Jul. 25, 2014.

International Search Report and Written Opinion of the International Searching Authority, or the Declaration issued in corresponding IA No. PCT/US2012/065014 dated Feb. 15, 2013.

International Search Report and Written Opinion of the International Searching Authority, or the Declaration issued in corresponding IA No. PCT/US2015/033689 dated Sep. 8, 2015.

International Search Report and Written Opinion of the International Searching Authority, or the Declaration issued in corresponding IA No. PCT/US2015/034336 dated Mar. 23, 2016.

Invitation to Pay Additional Fees issued in corresponding IA No. PCT/US2012/022162 dated Apr. 12, 2012.

Yue, et al., A novel polymeric chlorhexidine delivery device for the treatment of periodontal disease, Biomaterials, vol. 25, 2004, pp. 3743-3750.

International Search Report and Written Opinion, dated Sep. 19, 2014.

Search report issued in corresponding Chinese Application No. 201480019743.1 dated Jan. 17, 2018.

He et al., General Practitioner's Guidelines for Medication Use, Beijing Science and Technology Press, Nov. 30, 2010, 1205.

Avery Dennison Medical Solutions Demonstrates the Efficacy of its new Chlorhexidine Gluconate Adhesive Delivery System, Avery Dennison Medical Solutions, Sep. 13, 2011, 1-2.

Boddupalli, et al., Mucoadhesive drug delivery system: An overview, Jounal of Advanced Pharmaceutical Technology & Research, vol. 1, 2010, 381-387.

Search report issued in corresponding Chinese Application No. 201480019743.1 dated Feb. 5, 2018.

Pei, et al. "Plant Fiber Chemistry", pp. 244-246, China Light Industry Press, Jul. 2012.

"Giunchedi, et al. ""Formulation and in vivo evaluation of chlorhexidine buccal tablets prepared using drug-loaded chitosan microspheres,""" European Journal of Pharmaceutics and Biopharmaceutics, Elsevier

(56) References Cited

OTHER PUBLICATIONS

Science Publishers B.V., Amsterdam, NL, val. 53, No. 2, Mar. 1, 2002, pp. 233-239, XP004342819, ISSN: 0939-6411, DOI: 10.1016/S0939-6411(01)00237-5 Section 2.2 Preparation by spray-drying; table 2".
"International Search Report and Written Opinion issued in corresponding IA No. PCT/US2012/022162 dated Aug. 10, 2012."
Invitation to Pay Additional Fees issued in the corresponding IA No. PCT/US2012/022162 dated Apr. 12, 2012.
Maruzen, "New Experimental Chemistry Course 1 Basic Operation 1", Sep. 20, 1975, 459-463.
Yao, Application Directory of Pharmaceutical Excipients, China Medical Science and Technology Press, Aug. 31, 2011, 1342-1347.
Luo, et al., A Complete Collection of Pharmaceutical Excipients, Sichuan university of science and technology press, Jan. 31, 2006, 53-56.
International Search Report and Written Opinion dated Sep. 19, 2014 issued in corresponding IA No. PCT/US2014/015263 filed Feb. 7, 2014.
International Preliminary Report on Patentability dated Jul. 6, 2015 issued in corresponding IA. No. PCT/US2014/015263 filed Feb. 7, 2014.
Invitation to Pay Additional Fees dated May 22, 2014 issued in corresponding IA No. PCT/US2014/015263 filed Feb. 7, 2014.
International Preliminary Report on Patentability dated Sep. 24, 2015 issued in corresponding IA No. PCT/US2014/025549 filed Mar. 13, 2014.
International Preliminary Report on Patentability dated Jul. 23, 2013 issued in corresponding IA No. PCT/US2012/022162 filed Jan. 23, 2012.
International Search Report and Written Opinion dated Jan. 21, 2013 issued in corresponding IA No. PCT/US2012/037429 filed May 11, 2012.
International Preliminary Report on Patentability dated Nov. 19, 2013 issued in corresponding IA No. PCT/US2012/037429 filed May 11, 2012.
International Preliminary Report on Patentability dated May 20, 2014 issued In corresponding IA No. PCT/US2012/065014 filed Nov. 14, 2012.
Sateesh Kandavilli: "Polymers in Transdermal Drug Delivery Systems," Pharmaceutical Technology, May 31, 2002, XP055101101, Retrieved from the internet: http://www.pharamtech.com/pharmtech/data/articlestandard/pharmtech/192002/18600/article.pdf [retrieved on Feb. 10, 2014].
International Preliminary Report on Patentability dated Dec. 6, 2016 issued in corresponding IA No. PCT/US2015/034336 filed Jun. 5, 2015.
International Preliminary Report on Patentability dated Dec. 15, 2016 issued in corresponding IA No. PCT/US2015/033689 filed Jun. 2, 2015.

* cited by examiner

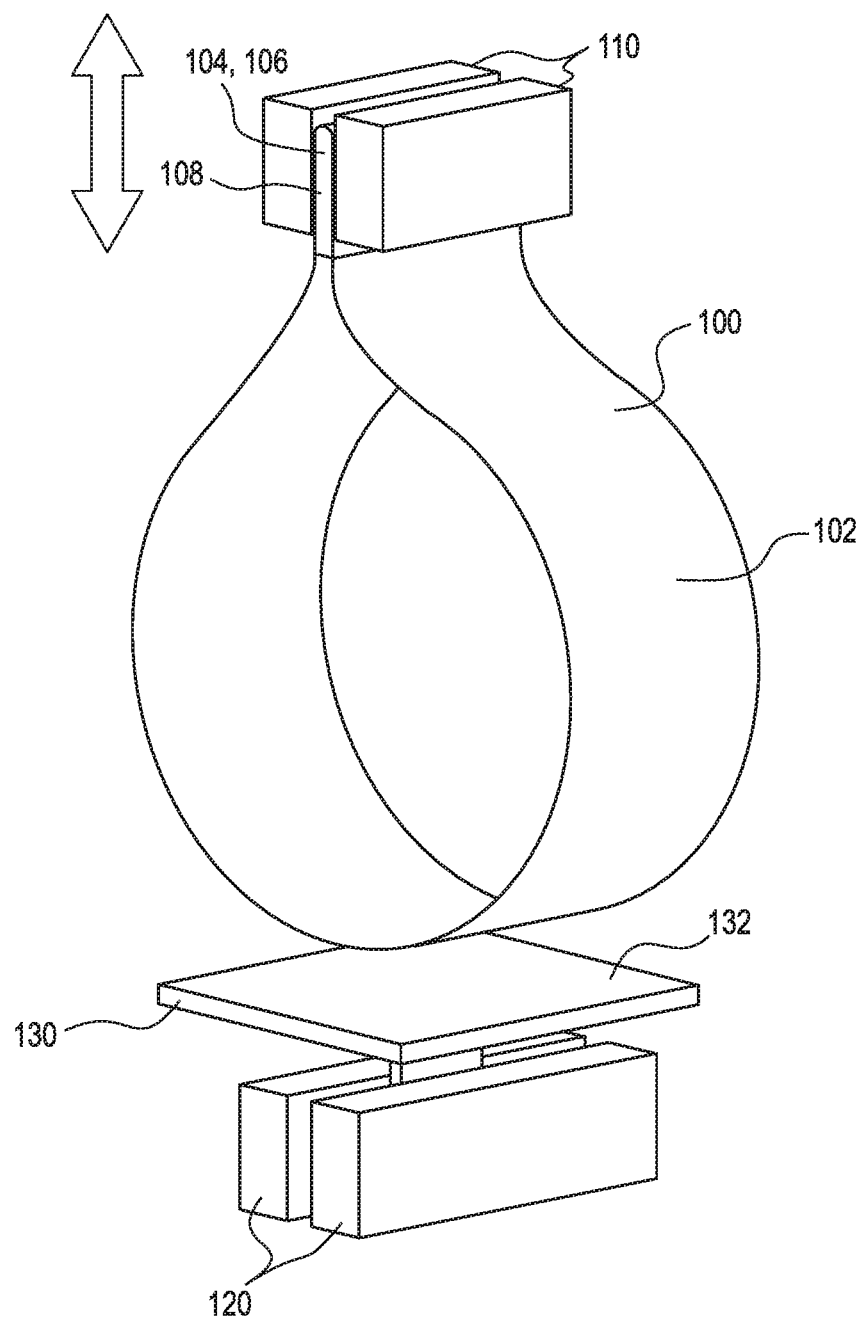

ANTIMICROBIAL ADHESIVES HAVING IMPROVED PROPERTIES

CROSS-REFERENCE TO RELATED APPLICATIONS

The present application is a divisional application of U.S. Utility patent application Ser. No. 14/766,524 filed Aug. 7, 2015, which is a 371 of International Application No. PCT/US14/15263 filed Feb. 7, 2014, which claims the benefit of U.S. Provisional Patent Application No. 61/761,838 filed Feb. 7, 2013 and U.S. Provisional Patent Application No. 61/790,692 filed Mar. 15, 2013, which are incorporated herein by reference in their entireties.

FIELD

The present subject matter relates to adhesives having antimicrobial properties and which exhibit relatively good stability, have improved release properties that promote antimicrobial efficacy, and which impart stability to certain antimicrobial agents incorporated in the adhesives. The adhesives also exhibit relatively high levels of fluid handling capacity.

BACKGROUND

Adhesives and particularly pressure sensitive adhesives are routinely used in conjunction with a wide array of medical articles to attach or retain articles to human skin. For application to the skin, fluid handling capacity of the adhesive should be sufficiently high so that the article can be maintained in place for an extended period of time without creating skin maceration and so that good adherence to the skin can be maintained.

Fluid handling capacity of an adhesive is a function of moisture vapor transmission rate (MVTR) and static absorption characteristics of the adhesive. Typically, maintaining a high fluid handling capacity can be achieved by varying both or only one of the two properties independently.

Antimicrobial adhesives are known. However, certain antimicrobial agents degrade into undesirable compound(s). Therefore, the composition and processing conditions of an antimicrobial adhesive are important to maintain stability and avoid generation of undesirable compounds. In certain applications, it is desirable that the adhesive achieve high antimicrobial efficacy in a short time frame correlating to their clinical use.

Adding antimicrobial agent within an adhesive typically impairs adhesion. Thus, in order to obtain sufficiently high antimicrobial efficacy and adhesive properties, the coat weight of the adhesive is increased. Increased coat weight yields higher antimicrobial concentration per surface area and promotes maintenance of adequate adhesion. However, increasing adhesive coat weight impairs the moisture vapor transmission rate and therefore the fluid handling capacity of the adhesive.

In order to obtain adequate antimicrobial efficacy, high concentrations of antimicrobial agents can be required. This tends to generate toxicity to the skin. It is therefore highly advantageous for antimicrobial adhesives to generate high log reduction of microbial activity throughout a 7 day period without generating cytotoxic side effects.

Certain antimicrobial agents, chlorhexidine being one of them, are unstable over time and/or at temperatures typically required to process solvent adhesives. The instability of chlorhexidine is evident by the generation of para chloroaniline or p-chloroaniline. It is therefore advantageous to formulate a chlorhexidine containing adhesive such that the adhesive exhibits stability over time and/or at typical processing temperatures, and maintains a relatively low content of p-chloroaniline.

In certain applications, it is desirable that the adhesives achieve relatively high release rates and/or extents of release of antimicrobial agents incorporated in the adhesive. High release rates and/or extents of release of antimicrobial agents in relatively short time periods can be a prerequisite for medical incise films or peripheral IV dressings, for example.

One of the challenges in developing antimicrobial adhesive is to achieve the right balance of antimicrobial concentration in the adhesive to get the right antimicrobial efficacy as well as maintain the right adhesive properties. When increasing the amount of antimicrobial agent in an adhesive the adhesive properties tend to decrease. It is therefore important to obtain relatively high release rates and high percentage of CHG release versus the content of antimicrobial agent in the adhesive. High antimicrobial efficacy and high CHG release ratio over relatively short time periods can be a prerequisite for medical incise films or peripheral IV dressings, for example.

Accordingly, adhesives which exhibit relatively high stability and antimicrobial efficacy and yet good fluid handling capacities are needed. Also, a need remains for an improved adhesive having enhanced release characteristics. In addition, strategies for achieving these somewhat offsetting or opposing characteristics are also needed.

SUMMARY

The difficulties and drawbacks associated with previously known adhesives and practices are addressed in the present compositions, methods and articles as follows.

In one aspect, the present subject matter provides an antimicrobial adhesive composition comprising chlorhexidine. The composition exhibits the following characteristics: (i) the adhesive composition inhibits microbial growth by more than 2 log throughout a 7 day contact time period, and (ii) the adhesive composition exhibits a grade 0 cytotoxcity.

In another aspect, the present subject matter provides an antimicrobial adhesive composition comprising chlorhexidine which exhibits the following characteristics: (i) after exposure to a temperature of 40° C. and a relative humidity of 75% for a time period of 6 months, the adhesive composition exhibits less than a 20% log reduction in antimicrobial efficacy, based upon an initial antimicrobial efficacy for at least one of the following microbes: *Escherichia coli*, methicillin-resistant *Staphylococcus aureus* (MRSA), *Candida albicans*, and vancomycin-resistant *Enterococcus fecium* (VRE).

In another aspect, the present subject matter provides an antimicrobial adhesive composition comprising chlorhexidine, which after exposure to a temperature of 40° C. and a relative humidity of 75% for a time period of 6 months, exhibits one of the following characteristics: (i) the composition is free of p-chloroaniline, or (ii) if p-chloroaniline is present in the composition, the concentration of p-chloroaniline is less than 1.0% by weight, percentage weight basis, based upon the initial weight of the chlorhexidine.

In another aspect, the present subject matter provides an antimicrobial adhesive composition comprising chlorhexidine which inhibits microbial growth by more than 2 log throughout a 7 day contact time period.

In yet another aspect, the present subject matter provides an antimicrobial adhesive composition comprising chlorhexidine gluconate which inhibits microbial growth by more than 2 log throughout a 7 day contact period, and which after exposure to a temperature of 40° C. and a relative humidity of 75% for a time period of 6 months, exhibits one of the following characteristics: (i) the composition is free of p-chloroaniline, or (ii) if p-chloroaniline is present in the composition, the concentration of p-chloroaniline is less than 1.0% by weight, percentage weight basis, based upon the initial weight of the chlorhexidine gluconate.

In yet another aspect, the present subject matter provides an antimicrobial adhesive composition comprising chlorhexidine gluconate which inhibits microbial growth by more than 2 log throughout a 7 day contact period, and which after exposure to a temperature of 40° C. and a relative humidity of 75% for a time period of 6 months, the adhesive exhibits a cytotoxicity grade of 0.

In still another aspect, the present subject matter provides a method of securing a medical article to biological skin and concurrently inhibiting microbial growth in a region of the securement. The method comprises providing an antimicrobial adhesive composition including at least one antimicrobial agent, wherein the adhesive composition exhibits at least one of properties (i) and (ii), property (i) being the composition inhibits microbial growth by more than 2 log throughout a 7 day contact period and property (ii) being the adhesive composition exhibits a stability characteristic such that after exposure to a temperature of 40° C. and a relative humidity of 75% for a time period of 6 months, the composition is free of p-chloroaniline or if p-chloroaniline is present, the concentration of p-chloroaniline is less than 1.0% by weight percentage weight basis, based upon the initial weight of the antimicrobial agent. The method also comprises applying the adhesive composition to a region of the medical article. And, the method additionally comprises securing the medical article to biological skin by contacting the adhesive composition applied to the medical article with the biological skin.

And, in yet another aspect, the present subject matter provides a medical article adapted for securing to biological skin and concurrently inhibiting microbial growth in a region of the securement. The article comprises an antimicrobial adhesive composition including at least one antimicrobial agent disposed on the face of the article. The adhesive composition exhibits at least one of properties (i) and (ii), property (i) being the composition inhibits microbial growth by more than 2 log throughout a 7 day contact period and property (ii) being the adhesive composition exhibits a stability characteristic such that after exposure to a temperature of 40° C. and a relative humidity of 75% for a time period of 6 months, the composition is free of p-chloroaniline or if p-chloroaniline is present, the concentration of p-chloroaniline is less than 1.0% by weight, percentage weight basis, based upon the initial weight of the antimicrobial agent.

In still another aspect, the present subject matter provides an antimicrobial adhesive composition which comprises at least one of chlorhexidine and chlorhexidine gluconate. The composition exhibits a cytotoxicity of grade 0 and a zone of inhibition of at least 0.5 mm, as described in greater detail herein.

In another aspect, the present subject matter provides an antimicrobial adhesive composition comprising from 25% to 98.99% of at least one adhesive component, from 0.01% to 15% of at least one antimicrobial agent, and from 1% to 60% of at least one disintegrant.

In another aspect, the present subject matter provides a method of enhancing release of an antimicrobial agent from an adhesive composition. The method comprises providing an adhesive composition including at least one antimicrobial agent. The method also comprises incorporating at least one disintegrant into the adhesive composition.

In still another aspect, the present subject matter provides medical articles that include an antimicrobial adhesive composition which comprises from 25% to 98.99% of at least one adhesive component, from 0.01% to 15% of at least one antimicrobial agent, and from 1% to 60% of at least one disintegrant.

In another aspect, the present subject matter provides an antimicrobial adhesive composition comprising an adhesive component, at least one antimicrobial agent, and at least one disintegrant, wherein the composition inhibits microbial growth more than 2 log after 6 hours contact.

As will be realized, the subject matter is capable of other and different embodiments and its several details are capable of modifications in various respects, all without departing from the subject matter. Accordingly, the description is to be regarded as illustrative and not restrictive.

BRIEF DESCRIPTION OF THE DRAWINGS

FIG. 1 is a schematic illustration of a loop tack testing configuration utilized in various evaluations described herein.

DETAILED DESCRIPTION OF THE EMBODIMENTS

The present subject matter relates to adhesive compositions that exhibit a unique combination of antimicrobial properties and stability. In many embodiments of the present subject matter, the compositions also exhibit a high fluid handling capacity as described herein. The adhesives of the present subject matter inhibit microbial growth by more than 2 log after contact, and for relatively long time periods such as over a time period of 7 days as described herein. In certain versions of the present subject matter, the compositions inhibit microbial growth by more than 2 log after 24 hours contact, and for relatively long time periods such as over a time period of 7 days as described herein. The adhesive compositions also exhibit relatively long shelf or storage lives such that after storage for a time period of 6 months or longer, the adhesives exhibit the noted antimicrobial properties. In certain versions, the compositions can be exposed to relatively high temperatures, e.g. up to 40° C. or 50° C., and relatively high moisture conditions, e.g. up to 75% relative humidity, for a time period of 6 months or longer; and still exhibit the noted antimicrobial properties. The present subject matter adhesives can be used in a wide range of applications and are particularly well suited for use in various medical applications such as skin-contacting adhesives.

Adhesive Compositions

Generally, the present subject matter adhesives are pressure sensitive adhesives (PSAs). Various PSAs can be used to form an adhesive layer on an article of interest or a portion of the article such as a backing layer to render the article adhesive. For example, PSAs may be formulated to offer good skin adhesion characteristics, offer excellent conformability, and provide a gentle release from the skin and wound site. The PSA layer can be continuous, discontinuous, pattern coated, or melt-blown, for example.

One well known means of identifying PSAs is the Dahlquist criterion. This criterion defines a PSA as an adhesive having a 1 second creep compliance of greater than $1\times10^{-6}$ cm²/dyne as described in *Handbook of PSA Technology*, Donatas Satas (Ed.), 2$^{nd}$ Edition, p. 172, Van Nostrand Reinhold, New York, N.Y., 1989. Alternatively, since modulus is, to a first approximation, the inverse of creep compliance, PSAs may be defined as adhesives having a Young's modulus of less than 1×10$^6$ dynes/cm². Another well known means of identifying a PSA is that it is aggressively and permanently tacky at room temperature and firmly adheres to a variety of dissimilar surfaces upon mere contact without the need of more than finger or hand pressure, and which may be removed from smooth surfaces without leaving a residue as described in *Glossary of Terms Used in the Pressure Sensitive Tape Industry* provided by the Pressure Sensitive Tape Council, 1996. Another suitable definition of a suitable PSA is that it preferably has a room temperature storage modulus within the area defined by the following points as plotted on a graph of modulus versus frequency at 25° C.: a range of moduli from approximately 2×10$^5$ to 4×10$^5$ dynes/cm² at a frequency of approximately 0.1 radians/sec (0.017 Hz), and a range of moduli from approximately 2×10$^6$ to 8×10$^6$ dynes/cm² at a frequency of approximately 100 radians/sec (17 Hz) (for example see FIG. 8-16 on p. 173 of *Handbook of PSA Technology* (Donatas Satas, Ed.), 2$^{nd}$ Edition, Van Nostrand Rheinhold, New York, 1989). Any of these methods of identifying a PSA may be used to identify suitable PSAs for use in accordance with the present subject matter.

The present subject matter adhesive compositions can include nearly any type of pressure sensitive adhesive component such as for example acrylic-based adhesives, silicone-based adhesives, rubber-based adhesives, polyurethane-based adhesives, and other types of adhesives and/or agents. These different types of adhesives are as follows.

The present subject matter also relates to adhesive compositions that exhibit enhanced release characteristics of actives and particularly of antimicrobial agents. As explained in greater detail herein, the adhesive compositions of the present subject matter utilize one or more disintegrants dispersed in the composition. In many embodiments of the present subject matter, the compositions also exhibit a high fluid handling capacity as described herein. As described in greater detail herein, the present subject matter provides pressure sensitive adhesive compositions comprising one or more pressure sensitive adhesive components, one or more disintegrants, one or more antimicrobial agents, and also one or more optional ingredients. In certain embodiments, upon exposure to water or moisture, the adhesive compositions rapidly release the antimicrobial agents. The present subject matter adhesives can be used in a wide range of applications and are particularly well suited for use in various medical applications such as skin-contacting adhesives.

Table 1 set forth below, lists typical and particular proportions for components in the adhesive compositions of the present subject matter.

TABLE 1

Adhesive Compositions

| Component | Typical Weight Percentage | Particular Weight Percentage |
|---|---|---|
| Adhesive Component(s) | 25-98.99% | 55-79.9% |
| Antimicrobial Agent(s) | 0.01-15% | 0.1-5% |
| Disintegrant(s) | 1-60% | 15-45% |

Each of the components in Table 1 is described in greater detail herein. All percentages noted herein are weight percentages unless noted otherwise.

1. Acrylic-Based Adhesives

The acrylic adhesive for use in the present subject matter is typically a solvent-based acrylic adhesive and may be any pressure sensitive acrylic adhesive that is capable of adhering to mammalian skin and that is free of ingredients known to cause undue irritation or toxicity to mammals. These adhesives typically include one or more acrylate copolymers.

Useful acrylate copolymers may or may not be self-crosslinking and are formed from at least two monomers chosen from: (1) hydroxyalkyl esters of acrylic or methacrylic acid in which the alkyl group comprises 2 to 4 carbon atoms, such as 2-hydroxyethyl acrylate, 2-hydroxyethyl methacrylate, 2-hydroxypropyl acrylate and 2-hydroxypropyl methacrylate; (2) alkyl esters of acrylic or methacrylic acid in which the alkyl group of the ester comprises 4 to 18 carbon atoms, such as n-butyl acrylate or methacrylate, isopropyl acrylate or methacrylate, n-hexyl methacrylate and 2-ethylhexyl acrylate; (3) α,β-unsaturated monocarboxylic or dicarboxylic acids, their anhydrides and their alkyl or alkenyl esters in which the alkyl group contains from 1 to 3 carbon atoms and the alkenyl group contains from 2 to 5 carbon atoms, such as acrylic acid, itaconic acid, maleic acid, maleic anhydride, alkyl methacrylate and the diethyl esters of fumaric or maleic acid; (4) vinyl monomers, such as vinyl acetate, acrylonitrile, vinyl propionate, vinylpyrrolidone and styrene; (5) monomers containing a functional group selected from amido, amino and epoxy groups, for example, acrylamide, N-butylacrylamide, alkylaminoalkyl and aminoalkyl derivatives of acrylic or methacrylic acid, such as amino-ethyl acrylate, aminoethyl methacrylate and 2-(dimethylamino) ethyl methacrylate, glycidyl methacrylate and glycidyl acrylate; (6) alkoxyalkyl esters of acrylic or methacrylic acid, for example methoxyethyl acrylates or methacrylates, butoxyethyl acrylates or methacrylates, methoxypropylene glycol acrylates or methacrylates and methoxypolyethylene glycol acrylates or methacrylates; and (7) hexamethylene glycol dimethacrylate.

As these copolymers can be self-crosslinking, they may also contain a crosslinking agent selected from those generally used by those skilled in the art, for example, organic peroxides, polyisocyanates, chelates or metals such as titanium or aluminum, or metal acetylacetonates, such as those of zinc, magnesium and aluminum.

These adhesive acrylate copolymers may take the form of solutions in a solvent system including a single organic solvent or a mixture of several solvents, which contain about 25% to about 55% by weight copolymers. Examples of suitable solvents include aromatic solvents such as toluene, xylene, etc. Suitable aliphatic solvents include esters such as ethyl acetate, propyl acetate, isopropyl acetate, butyl acetate, etc.; ketones such as methyl ethyl ketone, acetone, etc.; and aliphatic hydrocarbons such as heptanes, hexane, pentane, etc.

2. Silicone-Based Adhesives

Silicone PSAs include two major components, a polymer or gum, and a tackifying resin. The polymer is typically a high molecular weight polydimethylsiloxane or polydimethyldiphenylsiloxane, that contains residual silanol functionality (SiOH) on the ends of the polymer chain, or a block copolymer including polyorganosiloxane soft segments and urea terminated hard segments. The tackifying resin is generally a three-dimensional silicate structure that is end-capped with trimethylsiloxy groups (OSiMe$_3$) and also contains some residual silanol functionality. Examples of tackifying resins include SR 545, from General Electric Co., Silicone Resins Division, Waterford, N.Y., and MQD-32-2 from Shin-Etsu Silicones of America, Inc., Torrance, Calif. Manufacture of typical silicone PSAs is described in U.S. Pat. No. 2,736,721 (Dexter). Manufacture of silicone urea block copolymer PSA is described in U.S. Pat. No. 5,214,119 (Leir et al.) for example.

3. Rubber-Based Adhesives

Examples of rubber-based adhesives may include those comprising solid rubbers such as linear or radial A-B-A block copolymers or mixtures of these A-B-A block copolymers with simple A-B block copolymers. However, the proportion of A-B block copolymers, relative to the A-B-A block copolymers, should not normally exceed 85% by weight of the (total) block copolymers. In one embodiment, the proportion is in the range from about 35 to about 85% by weight of the block copolymers, and in another embodiment, the proportion is from about 55 to about 75% by weight of the block copolymers. In one embodiment, lower amounts such as 10 to 35% by weight of the block copolymers are used. These block copolymers can be based on styrene-butadiene, styrene-isoprene, and hydrogenated styrene-diene copolymers such as styrene ethylene-butylene. Suitable styrene-diene copolymers are exemplified by a blend of linear styrene-isoprene-styrene triblock copolymer and linear styrene-isoprene diblock copolymer. Such a material is available from Kraton Polymers as KRATON® D-1161 K and has a bound styrene content of about 15% and a diblock content of 17%. A second example is a blend of linear styrene-isoprene-styrene triblock copolymer and linear styrene-isoprene diblock copolymer available from Shell Chemical as KRATON® D-1117 and which has a bound styrene content of about 17% and a diblock content of 33%.

An example of a suitable hydrogenated styrene-diene copolymer is a thermoplastic elastomer comprising a blend of clear linear triblock and diblock copolymer-based on styrene and ethylene-butylene with a bound styrene of 14% mass. Such a material is commercially available from Shell Chemical Company as KRATON® G-1657. Another example is KRATON® G-1652 from Shell Chemical Company, which is a thermoplastic elastomer comprised of a clear linear triblock copolymer-based on styrene and ethylene-butylene, S-E/B-S, with a bound styrene content of about 30% by weight. Also suitable are polymers in which there is a combination of chemically saturated blocks and chemically unsaturated blocks. For example, a branched copolymer consisting of two polyisoprene chains attached to the rubber midblock of a styrene/ethylene-butylene/styrene triblock copolymer. Such a material, for example, is available from Shell Chemical Company having a styrene content of 18%, and isoprene content of 36% and an ethylene-butylene content of 46% by weight. Also, a low styrene synthetic copolymer of butadiene and styrene, commonly called SBR rubber, can be used as a solid rubber.

In one embodiment, liquid rubbers may be added to the adhesive material to adjust or control the adhesive or other characteristics. Liquid rubbers useful in this embodiment of the present subject matter include synthetic liquid isoprene rubber, depolymerized natural rubber, various functionally terminated synthetic liquid isoprene-styrene rubbers and liquid isoprene rubbers, liquid isoprene-styrene copolymer, liquid isoprene-butadiene copolymer, liquid butadiene-styrene copolymer and hydrogenated versions of these materials such as liquid ethylene-propylene-styrene. These liquid rubbers are generally compatible with the solid rubber. The liquid rubbers typically have a molecular weight of 25,000 to 50,000, a glass transition temperature of less than −50° C., and a viscosity at 38° C. of 50 to 10,000 Pas. A block copolymer of styrene and isoprene having a styrene content of about 13% and an isoprene content of about 87%, a glass transition of about −60° C., a melt viscosity of about 240 Pas at 50° C. and which is commercially available from Shell Chemical Company as LIR310, is particularly useful in the practice of the subject matter. Within the adhesive material, in one embodiment, the weight ratio of solid rubber to liquid rubber is in the range from about 100:1 to about 1:2, and is varied in order to obtain the desired degree of adhesiveness and tackiness.

In one embodiment, the weight ratio of solid rubber to liquid rubber is in the range from about 50:1 to about 5:1, and in another embodiment, from about 20:1 to about 10:1.

Optionally, an elastomeric polymer such as butyl rubber or high molecular weight polyisobutylene may also be blended into the adhesive material. The optional butyl rubber may be used in the viscosity average molecular weight range of 200,000 to 600,000 and is exemplified by the grades Butyl 065 or Butyl 077, both available from Exxon Chemical. The optional high molecular weight polyisobutylene may be used in the viscosity average molecular weight range of 800,000 to 2,500,000 and is exemplified by the VISTANEX® MM series of products, available from Exxon Chemical, with the MM L-80 grade being a preferred grade for the optional high molecular weight polyisobutylene. The optional high molecular weight rubbers, blended as described herein, may be added in amounts suitable to modify various properties of the final formulation and may be from 0% to about 50% of the total weight of the adhesive material, and in one embodiment from about 0.5% to about 25% of the total weight of the adhesive material, and in one embodiment from about 5% to about 10% of the total weight of the adhesive material. The optional low molecular weight polybutenes and/or mineral oil may be added in amounts from 0% to about 20% of the weight of the adhesive material and in one embodiment from about 0.5% to about 10% of the total weight of the adhesive material, and in one embodiment from about 0.5% to about 5% of the total weight of the adhesive material.

4. Polyurethane-Based Adhesives

Another useful class of PSAs can include polyurethanes. Polyurethanes may be produced by reacting a polyisocyanate with a polyalcohol (polyol). As described herein, a polyisocyanate is a molecule with two or more isocyanate functional groups and a polyalcohol is a molecule with two or more hydroxyl functional groups. The reaction product is a polymer containing urethane linkages. The functional groups can be alkanes, esters, ethers, and other components.

Isocyanates can be classed as aromatic, such as diphenylmethane diisocyanate (MDI) or toluene diisocyanate (TDI); or aliphatic, such as hexamethylene diisocyanate (HDI) or isophorone diisocyanate (IPDI). An example of a polymeric isocyanate is polymeric diphenylmethane diisocyanate, which is a blend of molecules with two-, three-, and four- or more isocyanate groups, with an average functionality of 2.7. Isocyanates can be further modified by partially reacting them with a polyol to form a prepolymer. A quasi-prepolymer is formed when the stoichiometric ratio of isocyanate to hydroxyl groups is greater than 2:1. A true prepolymer is formed when the stoichiometric ratio is equal to 2:1. Important characteristics of isocyanates include the molecular backbone, % NCO content, functionality, and viscosity.

Polyols are distinguished from short chain or low-molecular weight glycol chain extenders and cross linkers such as ethylene glycol (EG), 1,4-butanediol (BDO), diethylene glycol (DEG), glycerine, and trimethylol propane (TMP). Polyols are formed by base-catalyzed addition of propylene oxide (PO), ethylene oxide (EO) onto a hydroxyl or amine containing initiator, or by polyesterification of a di-acid, such as adipic acid, with glycols, such as ethylene glycol or dipropylene glycol (DPG). The choice of initiator, extender, and molecular weight of the polyol greatly affect its physical state, and the physical properties of the polyurethane polymer. Important characteristics of polyols include the molecular backbone, initiator, molecular weight, % primary hydroxyl groups, functionality, and viscosity. Examples of suitable polyurethanes adhesives include those described in U.S. Pat. No. 7,160,976 (Luhmann, et al.); U.S. Pat. No. 6,642,304 (Hansen, et. al); and U.S. Pat. No. 6,518,359 (Clemens et al.).

5. Other Agents

There can be included in the adhesive composition a wide array of additive materials. Fillers, tackifiers, antioxidants, stabilizers, and the like may be added to the formulate adhesive. Further, pharmaceutically active components, such as for example, anti-inflammatory agents, analgesic agents, anesthetics, or other pharmaceutically acceptable compounds, which do not affect the basic properties of the adhesive can be included in the adhesive layer in a pharmaceutically effective amount. Various pharmaceutically active agent(s) can be included in the adhesive composition such as inflammatory agents, analgesic agents, anesthetics, and combinations thereof.

Antimicrobial Agents

As used herein, the terms "antimicrobial" and "inhibiting microbial growth" describe the killing of, as well as the inhibition of or control of, the growth of bacteria, yeasts, fungi, and algae. Enhancement of antimicrobial efficacy refers to increasing the rate of kill and/or decreasing the amount of necessary antimicrobial agent to achieve antimicrobial control. The term "antimicrobial adhesive" means an adhesive that inhibits or decreases microbial growth by more than 2 log after contact, in certain versions of the present subject matter, more than 2 log after 24 hours, and in particular versions of the present subject matter, more than 2 log for a time period of 7 days at use concentrations of antimicrobial agent(s) of 0.01% to 15%. In certain versions of the present subject matter, the adhesive compositions inhibit or decrease microbial growth by more than 3 log after 3 days, and in particular versions of the subject matter, more than 3 log for a time period of 7 days, at use concentrations of one or more antimicrobial agents of 0.01% to 15%. The term "antimicrobial adhesive" also refers to the noted adhesives that inhibit or decrease microbial growth by more than 3 log, more particularly more than 3.5 log, and more particularly more than 6 log for the noted time periods. In particular versions of the present subject matter, the adhesive compositions inhibit or decrease microbial growth such as vancomycin-resistant *Enterococcus faecalis* (VRE) by more than 3.5 log and more particularly more than 5 log after 6 hours at use concentrations of one or more antimicrobial agents of 0.01% to 15%. In certain embodiments, the antimicrobial agent(s) are present in the adhesive compositions within a concentration range of from 0.5% to 5%.

Non-limiting examples of antimicrobial agents include diiodomethyl-para-tolylsulfone (DIMTS, Amical®), orthophenylphenol (OPP), sodium pyrithione (NaPT), zinc pyrithione (ZPT), 3-iodo-2-propynylbutylcarbamate (IPBC), 2-methyl-4-isothiazolin-3-one (MIT), 1,2-benzisothiazolin-3-one (BIT), 2-n-octyl-4-isothiazolin-3-one (OIT), 1-(3-chloroallyl)-3,5,7-triaza-1-azoniaadamantane chloride (CTAC, Dowicil 200), 2-(4-thiazolyl)-benzimidazole (TBZ, thiabendazole), β-bromo-β-nitrostyrene (BNS), 2,4,4'-trichloro-2-hydroxyphenyl ether (Triclosan), chloroxylenol (PCMX), chlorocresol (PCMC), para-tert-amylphenol (PTAP), N-(4-chlorophenyl)-N'-(3,4-dichlorophenyl)-urea (Trichlocarban), para-hydroxybenzoic acid esters (parabens), and mixtures thereof. A partial listing of preferred antimicrobial agents are DIMTS, OPP, NaPT, ZPT, IPBC, BIT, OIT, TBZ, BNS, 2,4,4'-trichloro-2-hydroxyphenyl ether, chloroxylenol, chlorocresol, PTAP, N-(4-chlorophenyl)-N'-(3,4-dichlorophenyl)-urea, and mixtures thereof. As described in greater detail herein, in certain embodiments the antimicrobial agent is a bis-biguanide salt and particularly, chlorhexidine or a salt thereof.

Non-volatile, water-soluble antimicrobial agents include natural components including botanical compounds such as aloe, acids such as anisic acid, hydroxy acids such as lactic acid, polypeptides such as N-cocoyl-L-arginine ethyl ether DL-pyrrolidone carboxylate CAE, enzymes such as lactoperoxidase, polysaccharides such as chitosan and proteins such as ionic lysostaphin; synthetic components including metal salts such as copper acetate and silver sulfadiazine, phenol derivatives such as phenoxyethanol, sulfur-containing compounds such as mafenide acetate, surfactants such as Nonoxynol-9, aminoglycosides such as streptomycin, iodine complexes such as povidone-iodine, hydric solvents such as benzyl alcohol, alkyl guanidines such as dodecylguanidine hydrochloride (DGH), anionic polymers such as polystyrene sulfonate, cationic polymers such as polytrimethoxysilyl propyldimethyloctadecyl ammonium chloride (AEM 5700™) and cationic nitrogen-containing organic compounds such as bis-biguanide salts and quaternary ammonium salts such as poly[(dimethylimino)-2-butene-1,4-diyl-chloride] and [4-tris(2-hydroxyethyl)ammonio]-2-butenyl-w-[tris(2-hydroxyethyl)ammonio]dichloride available as Polyquaternium-1. In certain embodiments, it is contemplated that in addition to the metal salts noted herein, other metal salts with antimicrobial metallic ions, for example mercury, could be used and furthermore that nonmetallic ions having antibacterial properties could also be utilized. Additional examples of other quaternary ammonium compounds which may be used as antimicrobial agents include but are not limited to Cetremide, Domiphen Bromide, polymeric quaternaries, and iodophores such as Povidone Iodine.

Bis-biguanide salts include hexamethylene biguanide hydrochloride (available as Vantocil IB®), polyhexamethylene biguanide hydrochloride (also known as PHMB, available as Cosmocil CQ®), bis-biguanide alkanes and mixtures thereof. A preferred bis-biguanide salt is 1,1'-hexamethylene bis(5-(p-chlorophenyl)biguanide salt commonly known as chlorhexidine salt. This form includes chlorhexidine diacetate, chlorhexidine dihydrochloride, chlorhexidine diphosphanilate or chlorhexidine digluconate, mainly differing by their solubility profile in various solvents and their application. The most preferred chlorhexidine salt according to the present subject matter is chlorhexidine digluconate, i.e., chlorhexidine gluconate (CHG). The CHG can be present in an amount ranging from about 0.01%, and more particularly from 0.5% to about 85% by weight of total solids, more preferably from about 1.0% to about 75.0% by weight of total solids, and most preferably from about 1.0% to about 10.0% by weight of total solids. In certain embodiments, a proportion of 3.0% of the antimicrobial agent based upon the total weight of the adhesive composition has been found useful. It will be appreciated that the CHG can be present at concentrations greater than or less than any of these noted concentrations.

In one version of the present subject matter, the adhesive compositions exhibit antimicrobial efficacy against a broad spectrum of microbes. "Broad-spectrum" refers without limitation to gram-positive bacteria such as *Staphylococcus aureus* and *Enterococcus faecalis*, and gram negative bacteria such as *Escherichia coli* and *Pseudomonas aerignosa*, and clinical isolates such as methicillin-resistant *Staphylococcus aureus* (MRSA) and vancomycin-resistant *Enterococcus faecium* (VRE). The noted bacteria can typically be found in a hospital environment. Additional nonlimiting examples of additional microorganisms to which the present subject matter is directed include *Staphylococcus aureus, Candida albicans, Aspergillus brasiliensis, Enterococcus faecium*, and *Staphylococcus epidermis*.

Generally, the adhesive compositions can utilize one or more antimicrobial agents in concentrations of from about 0.01% to about 15%. More particularly, in certain versions of the present subject matter, the antimicrobial agent(s) are used at concentrations in a range of from 0.1% to 15%. Typical concentrations include 1%, 3%, and 5% for example. It is also contemplated to use concentrations of antimicrobial agents less than 1%, 3%, or 5%, or other levels. However, it will be appreciated that the present subject matter includes the use of concentrations less than 0.01% and greater than 15%.

Moisture Absorbing Agents

In certain versions of the present subject matter, the adhesive compositions also optionally comprise one or more moisture absorbing agents. A wide array of moisture absorbing agents are contemplated. Typically, in many embodiments the moisture absorbing agents include hydrocolloids and/or super absorbent polymers.

1. Hydrocolloids

The adhesive composition may include one or more hydrocolloids. The hydrocolloids enable the final composition to adhere to moist body surfaces. This phenomenon is termed "wet tack". One or more water swellable hydrocolloids may also be present. The hydrocolloid may be linear or crosslinked. Suitable hydrocolloids include synthetic hydrocolloids such as sodium carboxymethyl cellulose, and natural products such as gelatin, pectin, guar gum, locust bean gum, tragacanth gum, gum karaya, starches, gum arabic, alginic acid and its sodium and/or calcium salts. Other synthetic hydrocolloids such as polyvinyl alcohol, polyvinyl acetate, polyvinyl pyrollidone, polyacrylic acid, polyhydroxyalkyl acrylates, polyacrylamides, high molecular weight polyethylene glycols and polypropylene glycols are useful. Others hydrocolloids include crosslinked or crystalline sodium carboxymethyl cellulose, crosslinked dextran, starch-acrylonitrile graft copolymer, microcrystalline cellulose, croscarmellose sodium and sodium starch glycolate.

The hydrocolloid is typically in the form of particles and may for example have an average particle size of from about 1 micrometer (μm) to about 400 (μm). Typically, the particles have an average particle size of from about 20 μm to about 200 μm, and more particularly from 20 μm to 150 μm. In one embodiment, the particle size of the particles is less than 150 μm, or less than 100 μm.

In one embodiment, the adhesive comprises from about 10% to about 80% by weight of one or more hydrocolloids. In certain versions, the hydrocolloids may constitute from about 30% to about 60% of the adhesive weight.

2. Super Absorbent Polymer

The super absorbent polymer (SAP) useful in the adhesive compositions comprises a water-swellable, hydrogel-forming absorbent polymer capable of absorbing large quantities of liquids such as water, body fluids (e.g., urine, blood), and the like. Additionally, the SAP is capable of retaining such absorbed fluids under moderate pressures. Typically the SAP absorbs many times its own weight in water, for example at least 50 times, particularly at least 100 times, and more particularly at least 150 times its weight in water. Additionally, the SAP exhibits good saline fluid absorption under load and high saline fluid absorption capacity. Typically the SAP absorbs at least 10 times, particularly at least 30 times, and more particularly at least 50 times its weight in saline fluid. Even though the SAP is capable of absorbing many times its own weight in water and/or saline, it does not dissolve in these fluids.

The ability of the SAP to absorb water and/or saline fluid is related to the degree of crosslinking present in the SAP. Increasing the degree of crosslinking increases the SAP's total fluid holding capacity under load. The degree of crosslinking is generally optimized to obtain a composition in which the rate and amount of absorbency are optimized. Certain SAPs are at least 10%, more particularly from about 10% to about 50%, and more particularly from about 20% to 40% crosslinked. Examples of suitable SAPs include crosslinked and polymerized α,β-beta ethylenically unsaturated mono- and dicarboxylic acids and acid anhydride monomers including, e.g., acrylic acid, methacrylic acid, crotonic acid, maleic acid/anhydride, itaconic acid, fumaric acid, and combinations thereof.

Super absorbent polymers useful in the present subject matter include, e.g., crosslinked acrylate polymers, crosslinked products of vinyl alcohol-acrylate copolymers, crosslinked products of polyvinyl alcohols grafted with maleic anhydride, cross-linked products of acrylate-methacrylate copolymers, crosslinked saponification products of methyl acrylate-vinyl acetate copolymers, crosslinked products of starch acrylate graft copolymers, crosslinked saponification products of starch acrylonitrile graft copolymers, crosslinked products of carboxymethyl cellulose polymers and crosslinked products of isobutylene-maleic anhydride copolymers, and combinations thereof.

The super absorbent polymer(s) is typically in the form of particles and generally are spherical and have an average particle size of from about 1 micrometer (μm) to about 400 μm. Particularly the particles have an average particle size of from about 20 μm to about 200 μm, and more particularly from 20 μm to 150 μm. In one embodiment, the particle size of the particles is less than 150 μm, or less than 100 μm. Useful commercially available super absorbent particles include, e.g., sodium polyacrylate super absorbent particles available under the AQUA KEEP series of trade designations including, e.g., particles having an average particle size of from about 20 μm to about 30 μm available under the trade designation AQUA KEEP 1 OSH-NF, particles having an average particle size of from 200 μm to 300 μm available under the trade designation AQUA KEEP 10SH-P, particles having an average particle size of from 320 μm to 370 μm available under the trade designation AQUA KEEP SA60S, particles having an average particle size of from 350 μm to 390 μm available under the trade designations AQUA KEEP SA60SX, SA55SX π and SA 60SL II, and particles having an average particle size of from 250 μm to 350 μm available under the trade designation AQUA KEEP SA60N TYPE II from Sumitomo Selka Chemicals Col, Ltd. (Japan). Also available super absorbent materials are Luquasorb 1010 and Luquasorb 1030 from BASF, Ludwigshafen, Germany.

In one embodiment, the adhesive contains about 10% by weight to about 80% by weight of a super absorbing polymer. In another embodiment, the adhesive contains about 30% to about 60% by weight of a super absorbing polymer.

3. Disintegrants

The adhesives of the present subject matter also comprise one or more disintegrants.

Disintegrants are agents added to compositions to promote the breakup or disintegration of the composition into smaller fragments in an aqueous environment thereby increasing the available surface area and promoting a more rapid release of one or more active agents or substances contained in the composition.

There are three major mechanisms and factors affecting composition disintegration as follows. Disintegration can occur as a result of swelling, porosity and/or capillary action, and/or deformation.

Although not all effective disintegrants swell in contact with water, swelling is believed to be a mechanism in which certain disintegrating agents such as starch for example, impart the disintegration effect. By swelling in contact with water, the adhesiveness of other ingredients in a composition are overcome thereby causing the composition to break up, disunite, or otherwise come apart.

Effective disintegrants that do not swell are believed to impart their disintegrating action through porosity and capillary action. Composition porosity provides pathways for the penetration of fluid into the composition. In certain systems, the disintegrant particles (with low cohesiveness and compressibility) themselves act to enhance porosity and provide these pathways into the composition. Liquid is drawn up or "wicked" into these pathways through capillary action and rupture the interparticulate bonds causing the composition to break apart.

It is believed that no single mechanism is responsible for the action of most disintegrants. But rather, it is more likely the result of inter-relationships between these major mechanisms.

A wide array of disintegrants can be used in the present subject matter compositions. Nonlimiting examples of such disintegrants include starches as corn starch, potato starch, and modified starches thereof; sweeteners; clays, such as bentonite; microcrystalline cellulose; alginates; and gums such as agar, guar, locust bean, karaya, pectin, and tragacanth. Combinations of these and/or with other disintegrants can also be used. Additional disintegrants include but are not limited to inorganic substances such as the previously noted bentonites as well as salts, acetates, alkali metal carbonates/bicarbonates, and citric add. In addition to previously noted organic compounds such as starch and modified starch, and starch decomposition products can also be used. Additional non-limiting examples of other disintegrants include cellulose, cellulose ethers such as methylcellulose, hydroxypropylcellulose and carboxymethylcellulose; poly(meth)acrylates; polyvinylpyrrolidone and cross-linked polyvinylpyrrolidone; gelatins; and pectins. As previously noted, combinations of any of these agents can be used.

Disintegrants can be gelling or non-gelling. In a preferred embodiment, the disintegrant is non-gelling. In a particular embodiment, microcrystalline cellulose is at least one of the non-gelling disintegrants added to the composition.

It will be understood that the present subject matter is not limited to any of these particular disintegrants.

The disintegrant can be included in an amount that is effective to impart at least one of the aforementioned disintegrant properties. As noted in Table 1, the disintegrant(s) are incorporated in the adhesive compositions at a weight proportion of from about 1% to about 60%, and more particularly within a range of from 20% to 40%. Generally, the disintegrant(s) are uniformly dispersed within the composition. However, the present subject matter includes the use of non-uniform dispersions of the disintegrant(s). For example, for certain applications it may be advantageous to provide a relatively high concentration of disintegrant(s) along or proximate to a face of the adhesive layer, and a lower concentration of disintegrant(s) within other regions spaced from the contacting face of the adhesive. Adhesive layers having concentration gradients of disintegrants within the layer such as across a thickness of the layer are also included in the present subject matter.

Characteristics of Adhesive Compositions

In addition to exhibiting the previously noted antimicrobial properties, in particular embodiments of the present subject matter, the adhesive compositions also exhibit a relatively high fluid handling characteristic or ability. The characteristic of relatively high fluid handling ability is exhibited in one or more fashions as follows.

In one aspect, the relatively high fluid handling ability of the present subject matter adhesive compositions is indicated by the compositions exhibiting a static absorption of at least about 5 $g/m^2/24$ hours. In certain versions of the present subject matter, the adhesive compositions exhibit a static absorption of at least 10 $g/m^2 24$ hours; of at least 25 $g/m^2/24$ hours; of at least 50 $g/m^2/24$ hours; of at least 75 $g/m^2/24$ hours; and in certain embodiments at least 100 $g/m^2/24$ hours. A description of determining static absorption is provided herein under "Test Methods."

In another aspect, the relatively high fluid handling characteristics of the adhesive compositions is indicated by its moisture vapor transmission rate (MVTR). Generally, the MVTR of the present subject matter adhesive compositions is at least 400 $g/m^2/24$ hours. In certain embodiments of the present subject matter, the adhesive compositions exhibit MVTR values of at least 600 $g/m^2/24$ hours; at least 800 $g/m^2/24$ hours; at least 1000 $g/m^2/24$ hours; at least 1200 $g/fm/24$ hours; and in certain versions, greater than 1500 $g/m^2/24$ hours. A description of determining MVTR is provided herein under "Test Methods."

In certain versions of the present subject matter, the adhesive compositions exhibit a static absorption of at least 25 $g/m^2/24$ hours and an MVTR value of at least 400 $g/m^2/24$ hours.

Many of the adhesive compositions also exhibit particular types and/or levels of adhesive characteristics such as particular values associated with Peel on polyethylene (or "Peel on PE") and/or loop tack. The "Peel on PE" characteristic is an indication of the level of adhesion achieved by a layer of adhesive. A detailed description of a procedure for measuring Peel on PE is provided herein. Certain versions of the adhesive compositions of the present subject matter exhibit Peel on PE values of at least 0.5 N/inch, particularly at least 1.0 N/inch, and more particularly at least 2.0 N/inch.

The loop tack characteristic is another indication of the level of adhesion achieved by a layer of adhesive. A detailed description of a procedure for measuring loop tack is provided herein. Certain versions of the adhesive compositions of the present subject matter exhibit loop tack values of at least 1.0 N/inch, particularly at least 1.5 N/inch, and more particularly at least 2.0 N/inch.

Many of the adhesive compositions also exhibit particular types and/or levels of stability. It is known that chlorhexidine can degrade over time and particularly upon exposure to temperatures and humidity levels associated with typical ambient conditions or those associated with the human body. An undesirable phenomenon relating to degradation of CHG is that p-chloroaniline (PCA) (also known as 4-chloroaniline) can be produced. PCA is an organochlorine compound and is generally undesirable for use with medical products or in medical applications.

In accordance with the present subject matter, it has been discovered that chlorhexidine, when incorporated in adhesive compositions as described herein, exhibits remarkable stability and if degradation occurs, any PCA which may be produced, is at relatively low concentrations or amounts and/or after extended and relatively long periods of time. Specifically, adhesive compositions as described herein and which comprise CHG, after exposure to temperatures of at least 40° C. and in certain embodiments 50° C.; and exposure to a relative humidity of 75% for a time period of 6 months; do not contain more than 5.0% (percentage weight basis, based upon the initial weight of the CHG) of PCA. In particular embodiments, the adhesive compositions exhibit this noted stability and if containing p-chloroaniline, the concentration of such is less than 1.0%; more particularly less than 0.5%, more particularly less than 0.25%, and in certain versions less than 0.15%. In certain versions, the adhesives will be free of PCA after exposure to the noted temperatures and/or humidity. These remarkable stability characteristics enable the adhesive compositions to be used in a wide array of applications, articles, and to also be stored in view of the relatively long shelf life of the adhesive composition.

In certain versions, the adhesives exhibit antimicrobial action by inhibiting microbial growth more than 2 log, more particularly more than 3 log, more particularly more than 3.5 log, more particularly more than 4 log, and more particularly more than 5 log after 6 hours contact at the use concentrations noted herein.

The adhesive compositions of the present subject matter can be applied as coatings in a wide array of techniques known in the field of adhesives and medical articles. The adhesive coatings or layers can be continuous, noncontinuous, uniform, nonuniform or patterned. Typically, coatweights of from about 10 $g/m^2$ to about 500 $g/m^2$, with 100 $g/m^2$ being most typical, can be utilized. In certain versions of the present subject matter, the adhesive compositions are used at coatweights of less than or equal to 50 $g/m^2$.

Medical Articles

The adhesive compositions described herein can be used in association with a wide array of medical articles. Non-limiting examples of such articles include wound dressings, incise films, surgical dressings, medical tapes, athletic tapes, surgical tapes, sensors, electrodes, ostomy appliances or related components such as sealing rings, catheters, connector fittings, catheter hubs, catheter adapters, fluid delivery tubes, electrical wires and cables, negative pressure wound therapy (NPWT) components, surgical drains, wound draining components, IV site dressings such as peripheral IV dressings, prostheses, stoma pouches, buccal patches, transdermal patches, dentures, hairpieces, bandages, diapers, medical padding for example liposuction padding, hygiene pads, corn and callous pads, toe cushioning pads, and pads for protecting and cushioning tube sites such as tracheotomy tubes. The medical articles include one or more faces, regions and/or surfaces to which the adhesive compositions of the present subject matter are applied. Forming a layer, coating, or other region of adhesive on an article enables the article to be adhered to a wide range of surfaces, including skin. It will be understood that the present subject matter is not limited to any of these articles. Instead, the subject matter includes the use of the adhesive compositions with other articles besides those noted herein. The medical articles may also include one or more layers covering the adhesive layer or coating such as a release liner.

Methods

The present subject matter also provides methods of enabling use of an adhesive composition applied to biological skin for a prolonged period of time, for example at least 1 day, and in certain versions at least 3 days, and in still other versions at least 7 days. The methods involve incorporating one or more antimicrobial agents and optionally also including one or more moisture absorbing agents in an adhesive as described herein and in the proportions noted herein. The resulting adhesive composition can then be used as a skin-contacting adhesive to adhere an article to skin or other surface.

The present subject matter also provides methods of enhancing release of one or more antimicrobial and/or other agents from an adhesive composition by incorporating disintegrant(s) in the composition. The resulting adhesive composition can then be used as a skin-contacting adhesive to adhere an article to skin or other surface.

Additional Aspects

In addition to and/or instead of the previously noted properties relating to the stability of the adhesives and absence of any significant degradation of CHG into PCA, the present subject matter also provides adhesive compositions that exhibit particular combinations of properties. For example, various representative embodiments of the present subject matter are as follows.

In one embodiment, the present subject matter provides an antimicrobial adhesive composition comprising at least one antimicrobial agent. The adhesive composition inhibits microbial growth by more than 2 log after contact and the adhesive composition exhibits a static absorption of at least about 10 $g/m^2/24$ hours.

In another embodiment, the present subject matter provides an antimicrobial pressure sensitive adhesive composition comprising a solvent-based acrylic adhesive component and at least one antimicrobial agent dispersed in the adhesive component. The adhesive composition inhibits growth of at least one of methicillin-resistant *Staphylococcus aurens* (MRSA) and vancomycin-resistant *Enterococcus faecium* (VRE) by more than 2 log after contact, and the adhesive composition exhibits a static absorption of at least about 10 $g/m^2/24$ hours.

In still another embodiment, the present subject matter provides a medical article defining at least one region having an antimicrobial adhesive composition disposed in the at least one region. The antimicrobial composition comprises at least one antimicrobial agent. The adhesive composition inhibits microbial growth by more than 2 log after contact. The adhesive composition exhibits a static absorption of at least about 10 $g/m^2/24$ hours.

In still another embodiment, the present subject matter provides a method of securing a medical article to biological skin and concurrently inhibiting a microbial growth in a region of the securement. The method comprises providing antimicrobial adhesive composition including at least one antimicrobial agent. The adhesive composition inhibits microbial growth by more than 2 log after contact and the adhesive composition exhibits a static absorption of at least about 10 $g/m^2/24$ hours. The method also comprises applying the adhesive composition to a region of the medical article. And, the method additionally comprises securing the medical article to biological skin by contacting the adhesive composition applied to the medical article with a biological skin.

In yet another embodiment, the present subject matter provides an antimicrobial adhesive composition comprising chlorhexidine. Upon application of the adhesive to a substrate at a coat weight within a range of from 10 gsm to 300 gsm, the resulting layer of adhesive exhibits a zone of inhibition of at least 0.5 mm with regard to a wide array of microorganisms including *Escherichia coli, Staphylococcus aureus*, methicillin-resistant *Staphylococcus aureus* (MRSA), *Candida albicans, Aspergillus brasiliensis, Enterococcus faecium*, vancomycin-resistant *Enterococcus faecium* (VRE), and *Staphylococus epidermis*.

In still another embodiment, the present subject matter provides an antimicrobial pressure sensitive adhesive comprising chlorhexidine. The adhesive exhibits a Peel on polyethylene ("Peel on PE") of at least 0.5 N/inch and also inhibits growth of a wide array of microorganisms by more than 2 log after contact.

In another embodiment, the present subject matter provides an antimicrobial pressure sensitive adhesive comprising chlorhexidine which exhibits a loop tack greater than 1 N/inch and inhibits growth of a wide array of microorganisms by more than 2 log after contact.

In yet another embodiment, the present subject matter provides an antimicrobial adhesive comprising chlorhexidine which does not contain more than 5.0% (percentage weight basis based upon the initial amount of chlorhexidine), more particularly less than 1.0%, more particularly less than 0.5%, more particularly less than 0.25%, and more particularly less than 0.15% of p-chloroaniline after 6 months at 40° C. and 75% relative humidity.

In still another embodiment, the present subject matter provides an antimicrobial adhesive comprising chlorhexidine which inhibits growth of a wide array of microorganisms by more than 2 log after contact and over a 7 day period.

In yet another embodiment, the present subject matter provides an antimicrobial adhesive composition comprising chlorhexidine gluconate which exhibits antimicrobial efficacy and is stable after aging at 40° C. and in certain versions at 50° C. and 75% relative humidity. The adhesive composition inhibits growth of a wide array of microorganisms by more than 2 log after contact and over a 7 day period, after the noted aging. Specifically, even after aging at 40° C. or 50° C. and 75% relative humidity, the adhesive composition inhibits growth of a wide array of microorganisms by more than 2 log after contact and over a 7 day period.

In still another embodiment, the subject matter provides an antimicrobial adhesive composition that exhibits a grade 0 cytotoxicity and more than 2 log reduction throughout a 7 day contact period.

In another embodiment, the present subject matter provides an antimicrobial adhesive composition comprising chlorhexidine and/or chlorhexidine gluconate that exhibits a grade 0 cytotoxicity and a relatively high stability such that after exposure to a temperature of 40° C. and in ceratin versions at 50° C. for a time period of 6 months, the composition is free of p-chloroaniline, or if p-chloroaniline is present in the composition, the concentration of p-chloroaniline is less than 5.0% by weight, percentage weight basis, based upon the initial weight of chlorhexidine or chlorhexidine gluconate. In particular embodiments, the adhesive compositions exhibit this noted stability and if containing p-chloroaniline, the concentration of such is less than 1.0%; more particularly less than 0.5%, more particularly less than 0.25%, and in certain versions less than 0.15%.

In yet another embodiment, the present subject matter provides an antimicrobial adhesive composition that exhibits a grade 0 cytotoxicity and a zone of inhibition of at least 0.5 mm.

In yet another embodiment, the subject matter provides an antimicrobial adhesive composition comprising chlorhexidine which exhibits the following characteristics: (i) the adhesive composition inhibits microbial growth by more than 2 log throughout a 7 day contact time period, and (ii) the adhesive composition exhibits a grade 0 cytotoxicity.

And, in yet another embodiment, the present subject matter provides an antimicrobial adhesive composition comprising chlorhexidine which exhibits the following characteristics. After exposure to a temperature of 40° C. and in certain versions at 50° C. and a relative humidity of 75% for a time period of 6 months, the adhesive composition exhibits less than a 20% log reduction in antimicrobial efficacy, based upon an initial antimicrobial efficacy for at least one, and in certain embodiments for all of the following microbes: *Escherichia coli*, methicillin-resistant *Staphylococcus aureus* (MRSA), *Candida albicans*, and vancomycin-resistant *Enterococcus faecium* (VRE).

In yet another embodiment, the subject matter provides an antimicrobial adhesive composition comprising chlorhexidine gluconate which inhibits microbial growth by more than 2 log throughout a 7 day contact period, and which after exposure to a temperature of 40° C. and in certain versions at 50° C. and a relative humidity of 75% for a time period of 6 months, the adhesive composition exhibits a grade 0 cytotoxicity.

Test Methods

Various evaluations are described herein that further illustrate aspects and features of the present subject matter. A description of measurements and testing procedures referenced or used in the evaluations is as follows.

1. Fluid Handling Capacity

Fluid Handling Capacity is a measure of the combined ability of the adhesive composition to take up moisture and to evaporate such moisture to the environment. This measure is performed by laminating a sample of the adhesive cut to the size of a Paddington cup to the cup on the side having the rubber ring. The circular sealing ring is placed on the sample of the cup and the screws are secured. The cup is weighed (W1). The cup is then turned upside down and filled with 20 ml of a NaCl solution (0.9% wt in deionized water). The metal sealing plate is secured to the top side of the cup. The filled cup is weighed (W2). The cup is placed sample side down into an oven at 37° C. for 24 hours. After 24 hours, the cup is removed from the oven and allowed to cool to room temperature for 30 minutes. The cup is then weighed (W3). The metal sealing plate is removed and the cup is emptied. The cup is allowed to stand for 15 minutes on a tissue to remove the NaCl solution, and then weighed (W4). The test conditions are 23° C. (±2°) and 50% (±2%) relative humidity. The Moisture Vapor Transmission Rate (MVTR) equals (W2−W3)×1000. The Static Absorption equals (W4−W1)×1000. The Fluid Handling Capacity (FHC) in g/10 cm²/24 hours is determined as follows:

$$FHC=(W2-W3)+(W4-W1)$$

This fluid handling capacity test is described in European Standard EN13726.

2. Antimicrobial Efficacy

Antimicrobial efficacy was evaluated by the following test method. Square pieces of adhesive 3 cm×3 cm are aseptically cut. Bacteria are grown with TSA at 32.5° C.+/−2.5° C. for 18 to 24 hours and then harvested with 10% TSB to achieve a final concentration between $1.0\times10^7$ cfu/ml to $5.0\times10^7$ cfu/ml. Under a biological cabinet class 100, the 3 cm×3 cm adhesive films are inoculated with 150 µl of the prepared challenge organism to achieve an inoculum of $1.0\times10^6$ to $5.0\times10^6$ cfu of the samples. The inoculated samples are covered with a 2 cm×2 cm sterile film to assure that the innoculum is in intimate contact with the adhesive and that the innoculum does not spread beyond the edge of the test sample. The inoculated test sample is held at 37° C.+/−1° C. and 75% RH+/−5%. The identical procedure is performed on a placebo (identical adhesive as the adhesive containing the CHG except that it does not contain CHG).

At a determined contact time, both the placebo and innoculated samples are placed into 100 ml of D/E neutralization broth and sonicated for 10 minutes. Enumeration of the recovered microorganisms is performed by the pour plate method as follows:

10 ml aliquots are plated with TSA ($10^{-1}$ dilution)
1 ml aliquots are plated with TSA ($10^{-2}$ dilution)
0.1 ml aliquots are plated with TSA ($10^{-3}$ dilution)
10 µl aliquots are plated with TSA ($10^{-4}$ dilution)
1 µl aliquots are plated with TSA ($10^{-5}$ dilution)

$Log_{10}$ Reduction=$Log_{10}$ cfu from placebo at contact time–$Log_{10}$ cfu from test sample at contact time 3. Zone of Inhibition Test The zone of inhibition test as described herein is performed by preparing bacterial cultures. The cultures are grown with trypticase soy agar (TSA) at 32.5° C.+/−2.5° C. for 18 to 24 hours and then harvested with 0.85% physiological saline to achieve a microbial suspension having a concentration of colony forming unites (cfu) within a range of from $1.0\times10^8$ cfu/ml to $5.0\times10^8$ cfu/ml.

Enumeration of the challenge organism suspension of interest is performed by a ten fold serial dilution of the suspension in sterile 0.85 physiological saline. 2×1.0 ml aliquot from each dilution is plated on TSA. The number of colony forming units (cfu's) on each plate are counted and the mean CFU/ml is determined, which represents the concentration of the challenge organism.

The concentration of the challenge organism is diluted at a ratio of 1:1000. After dilution, a sterile swab is used to apply the diluted solution to a TSA recovery plate. Application of 0.1 ml of the diluted suspension of the challenge organism is performed by streaking the surface of the TSA plate both horizontally and vertically.

A disc or circle shaped sample containing the adhesive composition to be evaluated is obtained or formed. The disc has a diameter of 8 mm. The adhesive disc sample is positioned in the center of the TSA recovery plate. An adhesive force contacts the surface of the TSA plate. The recovery plate(s) and adhesive samples are incubated for 24 hours at a temperature within a range from 30° C. to 35° C. Upon inspection, the diameter of the zone which is free of bacteria (or the microorganism of interest) is measured. This is the "zone of inhibition" as referred to herein.

4. Cytotoxicity

Cytotoxicity was evaluated as follows. L-929 mouse fibroblasts are incubated in 10 cm² wells to obtain subconfluent monolayer of cells. The growth medium was replaced in each well by 2 ml of agarose. Test articles prepared in a square were placed on the solidified agarose surface. The wells were incubated for a period of 24 hours and then observed under a microscope. Scoring for cytotoxicity is based on the following criteria, in Table 2.

TABLE 2

Cytotoxicity Scoring

| Grade | Reactivity | Condition of cultures |
|---|---|---|
| 0 | None | No detectable zone around or under specimen |
| 1 | Slight | Some malformed or degenerated cells under specimen |
| 2 | Mild | Zone limited to area under specimen |
| 3 | Moderate | Zone extending specimen size up to 1.0 cm |
| 4 | Severe | Zone extending farther than 1. cm beyond specimen |

5. Peel on Polyethylene

ASTM D1000-10 describes standard test methods for pressure sensitive adhesive coated tapes. These methods describe procedures in which adhesive tape samples are contacted with steel panels. In the present Peel on polyethylene (or "Peel on PE") evaluation, the steel panel was replaced with a polyethylene foil (25 µm) available from ACE under the designation "Ref 7660". The standard PE testing side is typically an interior face of the roll. The test material and the polyethylene substrate are conditioned for 24 hours at a temperature of 23° C.+/−2° C. and a relative humidity of 50%+/−2%.

Test assemblies are prepared by laminating a transfer tape onto a 4 inch by 4 inch aluminum plate. A hard rubber roller is used to ensure contact between the tape and the plate. The polyethylene foil (ACE Ref. 7660) is then laminated onto the tape adhered to the aluminum plate. The female side of the polyethylene film is used for testing.

A test specimen is cut in the machine direction to have a width of 25 mm and a length of approximately 150 mm. The cut specimen(s) is placed on the polyethylene foil and contacted therewith. A 4.5 pound roller is used to promote contact between the test specimen and polyethylene face of the foil. The roller is passed 2 times on top of the samples at a speed of about 300 mm/min. The adhered samples are left to rest for 20 minutes. After 20 minutes, the samples are peeled from the polyethylene foil using a peel tester at a 90 degree angle and a speed of 300 mm/min. Measurement of the maximum tensile force encountered during peel removal is measured.

6. Loop Tack Measurement

Loop tack measurement is generally performed in accordance with standard FTM9 "Loop Tack Measurement." Prior to the loop tack measurement, the test specimens or material(s) and glass substrates are conditioned for 24 hours at a temperature of 23° C.+/−2° C. and a relative humidity of 50%+/−2%. The test specimens are cut or otherwise sectioned to dimensions of 25 mm by 150 mm. Release liner(s), if present, are removed from the cut samples to reveal the adhesive face. Prior to testing, a cut sample is formed into a loop such that the exposed adhesive face is directed outward, and the two ends of the strip contact one another. FIG. 1 schematically depicts a loop tack testing configuration in which a specimen to be tested is positioned between upper and lower jaws 110, 120, respectively, of a peel tester apparatus. Specifically, a strip 100 having an adhesive face 102 is formed into a closed loop by contacting opposite ends 104, 106. The ends 104, 106 are covered with a polymeric cover material 108 to protect the jaws of the peel tester from the adhesive. The covered ends 104, 106 are positioned in, or otherwise engaged with, the upper jaws 110 of the peel tester. Engaged with the bottom or lower jaws 120, is a "float process" glass plate 130 having an upwardly directed glass face 132. The glass plate is typically square with sides of 25 mm. The glass plate 130 and particularly the glass face 132 is cleaned prior to testing to ensure a clean glass surface to which is contacted the adhesive face 102 of the strip 100.

Upon initiation of testing, the looped strip 100 is moved toward the face 132 of the glass plate 130 at a linear speed of 300 mm/min. As the adhesive face 102 of the looped strip 100 contacts the glass face 132, the area of contact increases until the entire upwardly directed face 132 of the glass plate is contacting the adhesive face 102 of the looped strip 100. When full contact with the glass has been achieved, i.e. the contact area is 25 mm by 25 mm, the direction of travel of the upper jaws 110 is reversed. Thus, the upper jaws 110 engaged with the ends 104, 106 of the looped strip 100, travel at a linear speed of 300 mm/min away from the lower jaws 120. As the jaws 110, 120 continue to separate from one another, the maximum tensile force measured between the adhesive face 102 of the looped strip and the face 132 of the glass plate 130 to achieve complete separation is measured.

7. Degradation of CHG to PCA

As described herein, chlorhexidine (CHG) can degrade into p-chloroaniline (PCA). As previously described herein, aging is typically performed at a temperature of 40° C. or 50° C., at a relative humidity of 75%, and for a time period of 6 months. Measurement of such degradation is performed as follows. Aged samples containing CHG, such as the antimicrobial adhesives described herein, are cut or formed into squares having dimensions of 4.4 cm by 4.4 cm (to provide a face surface area of 19.36 cm$^2$).

An adhesive film square is dissolved or diluted in a mixture of acetonitrile and buffer solution for subsequent extraction.

PCA is separated on a phenyl bonded reversed-phase column (Zorbax Eclipse XDB-phenyl, 150 mm×4.6 mm, 5 μm reference: agent 993967-612) using a secondary mobile phase (buffer solution/acetonitrile) running in gradient mode. Detection is carried out by UV light at 239 nm. Detection of PCA can be performed by high performance liquid chromatography (HPLC). Typical parameters for such analysis include detection at 239 nm, and an injection volume of 50 ml.

Preparation of the mobile phase A is as follows. 9.6 g of anhydrous monosodium phosphate (NaH$_2$PO$_4$) is added to a 1000 ml volumetric flask (solution 0.08 M) with about 950 ml ultrapure water and 5 ml triethylamine (TEA). The flask is agitated until complete dissolution occurs. The pH is adjusted to 3.0 with phosphoric acid (85%) and ultrapure water is then added to complete to 1000 ml volume. The solution is then filtered on a HVLP filter (or equivalent) and subjected to sonication for 15 minutes.

The mobile phase B is acetonitrile. Solvent dilution of mobile phase A to B is 68/32 (volume basis).

Representative partition characteristics of phases A and B in the noted column are as follows in Table 2:

TABLE 2

Representative Partition Characteristics

| Time (min) | Flow Rate (ml/min) | Phase A (%) | Phase B (%) |
| --- | --- | --- | --- |
| Initial | 0.60 | 77 | 23 |
| 14 | 0.60 | 72 | 28 |
| 20 | 0.60 | 72 | 28 |
| 27 | 0.60 | 68 | 32 |
| 29 | 1.00 | 40 | 60 |
| 35 | 1.00 | 40 | 60 |

TABLE 2-continued

Representative Partition Characteristics

| Time (min) | Flow Rate (ml/min) | Phase A (%) | Phase B (%) |
| --- | --- | --- | --- |
| 37 | 1.00 | 77 | 23 |
| 42 | 0.60 | 77 | 23 |

In the noted HPLC analysis, the column temperature is 35° C.; auto sampler temperature is 5° C.; and analysis time is 42 minutes. The retention time of PCA was determined to be 12.2 minutes. And the retention time of CHG was determined to be 16.8 minutes.

8. Antimicrobial Elution

Adhesive prepared are laminated between a stiff polyester and a 5 g/m2 polyester non woven. This allows the adhesive to remain unfolded and un-sticky during the test. Samples 2"×¾" are place in 20 ml demi-water. At regular time point a 500 mcl of solution is removed and analyzed by UV-spectrophotometry. In the case of the CHG a 255 nm wavelengths was used to measure the CHG concentration.

Evaluations

An adhesive composition was evaluated with regard to its antimicrobial efficacy and fluid handling capacity and specifically, its static absorption. The adhesive composition contained a majority proportion, i.e. 66%, of a solvent-based acrylic adhesive commercially available under the designation 1807 from Avery Dennison; and 4% of the antimicrobial agent CHG. One of the samples included a hydrocolloid, carboxymethyl cellulose (CMC) commercially available from numerous suppliers under the designation A800. The CMC was used at a concentration of 30%. All percentages are percentages by weight based upon the total weight of the composition. In various trials, the adhesive was laminated onto a polyurethane film available from Exopack under the designation Inspire 2103.

Table 3 summarizes the results of the antimicrobial evaluations of the adhesive compositions.

TABLE 3

Antimicrobial Test Results
Batch EVP8533 containing chlorhexidine gluconate acrylic adhesive
Cytotoxicity grade: 0
PCA after 6 months at 40° C./75% RH: 0.12%
Antimicrobial efficacy

|  | 6 hours | 3 days | 7 days |
| --- | --- | --- | --- |
| MRSA (ATCC33591) | >5.00 | >5.00 | >5.00 |
| VRE (ATCC51575) | 2.64 | >5.00 | >5.00 |
| E. Coli (ATCC8739) | >5.00 | >5.00 | >5.00 |
| P. Aeruginosa (ATCC9027) | >5.00 | >5.00 | >5.00 |
| C. albicans (ATCC10231) | >5.00 | >5.00 | >5.00 |

| | |
| --- | --- |
| Peel on PE: | 1.0 N/Inch |
| Loop tack: | 5.8 N/25 mm |
| MVTR: | 2300 g/m$^2$/24 h |
| Static absorption | 700 g/m$^2$/24 h |
| Zone of inhibition | |
| MRSA (ATCC33591) | 5 mm |
| S. aureus (ATCC6534) | 2 mm |
| S. epidermidis (ATCC12228) | 9 mm |
| VRE (ATCC51575) | 3 mm |
| K. pneumoniae (ATCC4352) | 4 mm |
| C. albicans (ATCC10231) | 4 mm |

As evident from Table 3, the adhesive comprising both the hydrocolloid and the antimicrobial agent, each in the noted proportions, exhibited a relatively high static absorption and high degree of antimicrobial efficacy, i.e. greater than 2 log.

In order to assess the present subject matter, several additional samples were prepared, designated as "Sample A" and "Sample B." Each Sample A and B included a pressure sensitive adhesive component, commercially available from Henkel adhesives under the designation DURO-TAK®. Each Sample A and B also included a disintegrant commercially available from FMC BioPolymer under the designation AVICEL® PH105. AVICEL® PH105 is microcrystalline cellulose. The antimicrobial agent in each sample was chlorhexidine gluconate (CHG).

TABLE 4

Samples A-B

| | Sample | |
|---|---|---|
| Component | A | B |
| DURO-TAK ® 129A | 56% | 20% |
| AVICEL ® PH105 | 40% | 20% |
| CHG | 4% | 4% |

Antimicrobial efficacy of each of Samples A-B was then evaluated with regard to VRE. Table 4 summarizes log reductions at 6 hours, 1 day, and 3 days.

TABLE 5

Antimicrobial Efficacy of Samples A-B

| | Sample | |
|---|---|---|
| Time Period | A | B |
| 6 Hours | 5.43 | 5.05 |
| 1 Day | >5.82 | >5.82 |
| 3 Day | >5.91 | >5.91 |

The results set forth in Table 5 demonstrate the significant increase in antimicrobial efficacy against VRE at time periods of 6 hours, 1 day, and 3 days.

Several additional formulations were evaluated. Formulations AW22.13, AW29.13, AW 30.13, AW 31.13, SHC138.13, SHC139.13, SHC 140.13 were prepared with Avery Dennison adhesive 1807, a solvent-based acrylic adhesive, varying percentages of CHG, A800, and AVICEL® PH105. Tables 6 and 7 show CHG elution data for the formulations. Table 7 shows the antimicrobial efficacy log reduction.

TABLE 6

CHG Elution Data

| Formulation | Adhesive | CHG (%) | Avicel PH105 | CHG (mcg/cm$^2$) | Coat Weights (g) | CHG @30 min (mcg/cm2) | CHG @1 hour (mcg/cm2) | CHG @2 hours (mcg/cm2) | CHG @6 hours (mcg/cm2) | CHG Release @30 min (% w/w) | CHG Release @1 hour (% w/w) | CHG Release @2 hours (% w/w) | CHG Release @6 hours (% w/w) |
|---|---|---|---|---|---|---|---|---|---|---|---|---|---|
| AW22.13 | 1807 | 4 | 0 | 128.0 | 32.0 | 0.00 | 3.28 | 0.08 | 1.31 | 0.00 | 2.6 | 0.1 | 1.0 |
| | 1807 | 4 | 0 | 128.0 | 32.0 | 0.00 | 0.00 | 0.00 | 0.00 | 0.00 | 0.00 | 0.0 | 0.0 |
| | 1807 | 4 | 0 | 128.0 | 32.0 | 0.00 | 0.00 | 1.19 | 0.40 | 0.00 | 0.00 | 0.9 | 0.3 |
| AW29.13 | 1807 | 4 | 30 | 148.4 | 37.1 | 8.44 | 24.80 | 37.45 | 43.98 | 5.7 | 16.7 | 25.2 | 29.6 |
| | 1807 | 4 | 30 | 148.4 | 37.1 | 9.45 | 21.58 | 36.32 | 48.16 | 6.4 | 14.5 | 24.5 | 32.4 |
| | 1807 | 4 | 30 | 148.4 | 37.1 | 8.46 | 9.04 | 32.36 | 40.02 | 5.7 | 12.8 | 21.8 | 27.0 |
| AW30.13 | 1807 | 5 | 25 | 168.5 | 33.7 | 18.21 | 33.72 | 49.81 | 57.91 | 10.8 | 20.0 | 29.6 | 34.4 |
| | 1807 | 5 | 25 | 168.5 | 33.7 | 20.15 | 35.16 | 49.47 | 64.40 | 12.0 | 20.9 | 29.4 | 38.2 |
| | 1807 | 5 | 25 | 168.5 | 33.7 | 19.30 | 32.73 | 47.23 | 56.54 | 11.5 | 19.4 | 28.0 | 33.6 |
| AW31.13 | 1807 | 5 | 30 | 190.0 | 38.0 | 23.49 | 45.09 | 63.09 | 68.58 | 12.4 | 23.7 | 33.2 | 36.1 |
| | 1807 | 5 | 30 | 190.0 | 38.0 | 27.54 | 47.81 | 63.58 | 67.35 | 14.5 | 25.2 | 33.5 | 35.4 |
| | 1807 | 5 | 30 | 190.0 | 38.0 | 24.57 | 46.98 | 61.98 | 66.37 | 12.9 | 24.7 | 32.6 | 34.9 |
| SHC138.13 | 1807 | 2.5 | 20 | 95.0 | 38.0 | 0.00 | 2.73 | 9.22 | 11.49 | 0.00 | 2.9 | 9.7 | 12.1 |
| | 1807 | 2.5 | 20 | 95.0 | 38.0 | 0.00 | 3.18 | 6.84 | 12.73 | 0.00 | 3.3 | 7.2 | 13.4 |
| | 1807 | 2.5 | 20 | 95.0 | 38.0 | 0.00 | 1.76 | 6.26 | 12.20 | 0.00 | 1.9 | 6.6 | 12.8 |
| SHC139.13 | 1807 | 4 | 20 | 140.0 | 35.0 | 6.15 | 14.86 | 21.99 | 37.34 | 4.4 | 10.6 | 15.7 | 26.7 |
| | 1807 | 4 | 20 | 140.0 | 35.0 | 6.95 | 13.19 | 24.27 | 42.07 | 5.0 | 9.4 | 17.3 | 30.1 |
| | 1807 | 4 | 20 | 140.0 | 35.0 | 2.94 | 9.98 | 19.76 | 29.33 | 2.1 | 7.1 | 14.1 | 21.0 |
| SHC140.13 | 1807 | 5 | 20 | 175.0 | 35.0 | 13.36 | 26.15 | 33.35 | 45.84 | 7.6 | 14.9 | 19.1 | 26.2 |
| | 1807 | 5 | 20 | 175.0 | 35.0 | 18.80 | 30.44 | 42.71 | 51.50 | 10.7 | 17.4 | 24.4 | 29.4 |
| | 1807 | 5 | 20 | 175.0 | 35.0 | 15.06 | 27.41 | 35.47 | 45.23 | 8.6 | 15.7 | 20.3 | 25.8 |

TABLE 7

Additional CHG Elution Data

| Formulation | Adhesive | CHG (%) | AB00 (%) | Avicel PH105 | CHG (mcg/cm$^2$) | Coat Weights (g) | CHG @30 min (mcg/cm2) | CHG @1 hour (mcg/cm2) | CHG @2 hours (mcg/cm2) | CHG @6 hours (mcg/cm2) | CHG Release @30 min (% w/w) | CHG Release @1 hour (% w/w) | CHG Release @2 hours (% w/w) | CHG Release @6 hours (% w/w) |
|---|---|---|---|---|---|---|---|---|---|---|---|---|---|---|
| AW22.13 | 1807 | 4 | 30 | 0 | 400.0 | 100.0 | 16.62 | 25.08 | 29.56 | 29.21 | 4.2 | 6.3 | 7.4 | 7.3 |
| | 1807 | 4 | 30 | 0 | 400.0 | 100.0 | 21.87 | 28.64 | 30.38 | 30.15 | 5.5 | 7.2 | 7.5 | 7.5 |
| | 1807 | 4 | 30 | 0 | 400.0 | 100.0 | 18.79 | 27.21 | 29.43 | 29.92 | 4.7 | 6.8 | 7.4 | 7.5 |

TABLE 7-continued

Additional CHG Elution Data

| Formulation | Adhesive | CHG (%) | AB00 (%) | Avicel PH105 | CHG (mcg/cm²) | Coat Weights (g) | CHG @30 min (mcg/cm2) | CHG @1 hour (mcg/cm2) | CHG @2 hours (mcg/cm2) | CHG @6 hours (mcg/cm2) | CHG Release @30 min (% w/w) | CHG Release @1 hour (% w/w) | CHG Release @2 hours (% w/w) | CHG Release @6 hours (% w/w) |
|---|---|---|---|---|---|---|---|---|---|---|---|---|---|---|
| AW12.13 | 1807 | 4 | 0 | 30 | 400.0 | 100.0 | 47.47 | 78.60 | 103.60 | 102.53 | 11.9 | 19.7 | 25.9 | 25.6 |
| | 1807 | 4 | 0 | 30 | 400.0 | 100.0 | 49.33 | 89.03 | 107.91 | 101.13 | 12.3 | 22.3 | 27.0 | 25.3 |
| | 1807 | 4 | 0 | 30 | 400.0 | 100.0 | 48.40 | 82.72 | 105.69 | 107.27 | 12.1 | 20.7 | 26.4 | 26.8 |

TABLE 8

Additional Antimicrobial Efficacy Data

| | MRSA (ATCC33491) | | | E. coli (ATCC8739) | | | P. aeruginosa (ATCC9027) | | | C. albicans (ATCC10231) | | | A. brasiliensis (ATCC16404) | | |
|---|---|---|---|---|---|---|---|---|---|---|---|---|---|---|---|
| Formulation | 30 mins | 1 hour | 2 hours | 30 mins | 1 hour | 2 hours | 30 mins | 1 hour | 2 hours | 30 mins | 1 hour | 2 hours | 30 mins | 1 hour | 2 hours |
| AW 5.13 | 1.08 | | 3.57 | 0.96 | | 4.61 | 4.91 | | 5.39 | 0.96 | | 3.55 | 0.3 | | 0.41 |
| AW 29.13 | 3.99 | 5.77 | 5.77 | 1.55 | 2.98 | 4.49 | 3.41 | 5.22 | 5.22 | 1.55 | 4.24 | 5.68 | 0.59 | 0.69 | 0.83 |
| AW 30.13 | 2.87 | 4.97 | 5.77 | 2.65 | 2.79 | 5.05 | 4.76 | 5.22 | 5.22 | 2.65 | 3.08 | 5.68 | 0.56 | 0.74 | 0.72 |
| AW 31.13 | 5.25 | 5.77 | 5.77 | 1.72 | 4.07 | 5.32 | 5.09 | 5.22 | 5.22 | 1.72 | 5.25 | 5.68 | 0.56 | 0.78 | 0.79 |

The CHG adhesive delivery system inhibits microbial or bacterial growth underneath an adhesive article such as a dressing but does not inhibit such growth beyond the limit of the dressing. However, per opposition to the central antimicrobial pad area in the commercial CHG containing dressings, the entire dressing area of the CHG adhesive delivery system film dressing contains CHG creating a larger surface of antimicrobial protection; therefore, generating a zone of inhibition beyond the antimicrobial area becomes unnecessary.

In addition to its antimicrobial properties, the fluid handling characteristics of the CHG adhesive delivery system outperforms the NWPT drape and commercial hydrocolloid dressings. The CHG adhesive delivery system offers in addition static absorption properties which other NWPT drape or IV securement film dressings do not exhibit.

The CHG adhesive delivery system could be used for any application requiring infection prevention, moisture management and transparency such as the securement of IV catheters, surgical incise films or post-op dressing for example.

Many other benefits will no doubt become apparent from future application and development of this technology.

All patents, applications, articles, and standards noted herein are hereby incorporated by reference in their entirety.

As described hereinabove, the present subject matter solves many problems associated with previous compositions, strategies, systems and/or devices. However, it will be appreciated that various changes in the details, materials and arrangements of components and operations, which have been herein described and illustrated in order to explain the nature of the subject matter, may be made by those skilled in the art without departing from the principle and scope of the subject matter, as expressed in the appended claims.

What is claimed is:

1. An antimicrobial adhesive composition comprising chlorhexidine and at least one non-gelling disintegrant;
   wherein the adhesive composition inhibits microbial growth by more than 2 log throughout a 7-day contact time period;
   wherein the non-gelling disintegrant is microcrystalline cellulose; and
   wherein the non-gelling disintegrant is 15% to 45% of the antimicrobial adhesive composition;
   wherein the adhesive composition comprises at least one adhesive component selected from the group consisting of a solvent-based acrylic adhesive, a silicone-based adhesive, a rubber-based adhesive, a polyurethane-based adhesive, and combinations thereof; and
   wherein the adhesive composition exhibits a stability characteristic such that after exposure to a temperature of 40° C. and a relative humidity of 75% for a time period of 6 months, the composition is free of p-chloroaniline or if p-chloroaniline is present, the concentration of p-chloroaniline is less than 3.0% by weight, percentage weight basis, based upon the initial weight of the antimicrobial agent.

2. The adhesive composition of claim 1 wherein the adhesive composition exhibits a static absorption of at least about 5 g/m2/24 hours.

3. The adhesive composition of claim 1 wherein the adhesive composition also exhibits a moisture vapor transmission rate (MVTR) of at least 400 g/m2/24 hours.

4. An antimicrobial adhesive composition comprising:
   from 25% to 98.99% of at least one adhesive component;
   from 0.01% to 15% of at least one antimicrobial agent; and
   from 1% to 60% of at least one disintegrant;
   wherein the disintegrant is microcrystalline cellulose;
   wherein the antimicrobial agent is chlorhexidine salt; and
   wherein the at least one adhesive component is selected from the group consisting of a solvent-based acrylic adhesive, a silicone-based adhesive, a rubber-based adhesive, a polyurethane-based adhesive, and combinations thereof; and wherein the adhesive composition exhibits a stability characteristic such that after exposure to a temperature of 40° C. and a relative humidity of 75% for a time period of 6 months, the composition is free of p-chloroaniline or if p-chloroaniline is present, the concentration of p-chloroaniline is less than 3.0% by weight, percentage weight basis, based upon the initial weight of the antimicrobial agent.

5. The adhesive composition of claim 4 wherein the adhesive composition is a pressure sensitive adhesive.

6. The adhesive composition of claim 4 further comprising at least one agent selected from the group consisting of fillers, tackifiers, antioxidants, stabilizers, and combinations thereof.

7. The adhesive composition of claim 4 further comprising at least one pharmaceutically active agent.

8. The adhesive composition of claim 7 wherein the pharmaceutically active agent is selected from the group consisting of anti-inflammatory agents, analgesic agents, anesthetics, and combinations thereof.

9. The adhesive composition of claim 4 wherein the chlorhexidine salt is chlorhexidine digluconate (CHG).

10. The adhesive composition of claim 4 wherein the disintegrant is selected from the group consisting of starches, sweeteners, clays, cellulose, cellulose ethers, alginates, gums, salts, acetates, alkali metal carbonates, citric acid, poly(methyl) acrylates, polyvinylpyrrolidones, gelatins, pectins, and combinations thereof.

11. The adhesive composition of claim 10 wherein the disintegrant includes starches selected from the group consisting of corn starch, potato starch, modified starches, starch decomposition products, and combinations thereof.

12. The adhesive composition of claim 10 wherein the disintegrant includes gums selected from the group consisting of agar, guar, locust bean, karaya, pectin gum, tragacanth gum, and combinations thereof.

13. The adhesive composition of claim 10 wherein the disintegrant includes cellulose ethers selected from the group consisting of methylcellulose, hydroxypropyl cellulose, carboxymethyl cellulose, and combinations thereof.

14. The adhesive composition of claim 4 wherein the composition inhibits growth of vancomycin-resistant *Enterococcus faecalis* (VRE) by more than 3.5 log after 6 hours.

15. The adhesive composition of claim 4, wherein the disintegrant is non-gelling.

16. A medical article comprising the adhesive composition of claim 4.

17. An antimicrobial adhesive composition comprising an adhesive component, at least one antimicrobial agent, and at least one non-gelling disintegrant,
wherein the composition inhibits microbial growth more than 2 log after 6 hours contact;
wherein the non-gelling disintegrant is microcrystalline cellulose;
wherein the antimicrobial agent is chlorhexidine salt; and
wherein the adhesive component is selected from the group consisting of a solvent-based acrylic adhesive, a silicone-based adhesive, a rubber-based adhesive, a polyurethane-based adhesive, and combinations thereof; and
wherein the adhesive composition exhibits a stability characteristic such that after exposure to a temperature of 40° C. and a relative humidity of 75% for a time period of 6 months, the composition is free of p-chloroaniline or if p-chloroaniline is present, the concentration of p-chloroaniline is less than 3.0% by weight, percentage weight basis, based upon the initial weight of the antimicrobial agent.

18. The adhesive composition of claim 17 wherein the composition inhibits microbial growth more than 3 log after 6 hours contact.

19. The adhesive composition of claim 18 wherein the composition inhibits microbial growth more than 3.5 log after 6 hours contact.

20. The adhesive composition of claim 19 wherein the composition inhibits microbial growth more than 4 log after 6 hours contact.

21. The adhesive composition of claim 20 wherein the composition inhibits microbial growth more than 5 log after 6 hours contact.

22. The adhesive composition of claim 4, wherein the adhesive component is self-crosslinking.

* * * * *